(12) United States Patent
de la Rama et al.

(10) Patent No.: US 8,827,910 B2
(45) Date of Patent: Sep. 9, 2014

(54) MAGNETICALLY GUIDED CATHETER WITH FLEXIBLE TIP

(75) Inventors: Alan de la Rama, Cerritos, CA (US); Carlo Pappone, Lecco (IT); Peter Cheng Chen, Irvine, CA (US); Cary Hata, Irvine, CA (US); Jared A. Shimizu, Irvine, CA (US)

(73) Assignee: St. Jude Medical, Atrial Fibrillation Divsion, Inc., St. Paul, MN (US)

( * ) Notice: Subject to any disclaimer, the term of this patent is extended or adjusted under 35 U.S.C. 154(b) by 994 days.

(21) Appl. No.: 12/667,338

(22) PCT Filed: Jul. 3, 2008

(86) PCT No.: PCT/US2008/069248
§ 371 (c)(1),
(2), (4) Date: Jan. 20, 2011

(87) PCT Pub. No.: WO2009/023385
PCT Pub. Date: Feb. 19, 2009

(65) Prior Publication Data
US 2011/0118582 A1    May 19, 2011

Related U.S. Application Data

(63) Continuation of application No. 11/853,759, filed on Sep. 11, 2007, now Pat. No. 8,187,267.

(60) Provisional application No. 60/947,791, filed on Jul. 3, 2007, provisional application No. 60/939,799, filed on May 23, 2007.

(51) Int. Cl.
*A61B 8/14* (2006.01)
*A61B 5/04* (2006.01)
*A61M 31/00* (2006.01)
*A61B 18/18* (2006.01)
*A61B 18/14* (2006.01)
*A61B 18/00* (2006.01)
*A61B 17/00* (2006.01)

(52) U.S. Cl.
CPC ..... *A61B 18/1492* (2013.01); *A61B 2018/1465* (2013.01); *C08L 2201/12* (2013.01); *A61B 2018/00839* (2013.01); *A61B 2018/00029* (2013.01); *A61B 2018/00023* (2013.01); *A61B 2018/00351* (2013.01); *A61B 2017/00867* (2013.01)
USPC ........... 600/466; 600/381; 604/95.01; 606/46

(58) Field of Classification Search
CPC ................. A61B 18/1492; A61B 2017/00243; A61B 2018/00351; A61B 2018/00577; A61B 2018/00257; A61B 2018/00357; A61B 2018/1465; A61B 2018/1475
USPC ........................ 600/372–374, 381, 393, 466; 604/95.01; 606/41, 46
See application file for complete search history.

(56) References Cited

U.S. PATENT DOCUMENTS

| | | | |
|---|---|---|---|
| 4,325,374 A | 4/1982 | Komiya | |
| 5,163,905 A | 11/1992 | Don Michael | |
| 5,279,299 A | 1/1994 | Imran | |
| 5,378,230 A | 1/1995 | Mahurkar | |
| 5,462,521 A | 10/1995 | Brucker et al. | |
| 5,487,385 A | 1/1996 | Avitall | |
| 5,545,200 A | 8/1996 | West et al. | |
| 5,681,280 A | 10/1997 | Rusk et al. | |
| 5,800,428 A | 9/1998 | Nelson et al. | |
| 5,833,632 A | 11/1998 | Jacobsen et al. | |
| 5,902,328 A | 5/1999 | Lafontaine et al. | |
| 5,919,188 A | 7/1999 | Shearon et al. | |
| 5,951,471 A | 9/1999 | De la Rama et al. | |
| 5,992,418 A | 11/1999 | de la Rama et al. | |
| 6,001,095 A | 12/1999 | de la Rama et al. | |
| 6,017,338 A | 1/2000 | Brucker et al. | |
| 6,030,382 A | 2/2000 | Fleischman et al. | |
| 6,053,912 A | 4/2000 | Panescu et al. | |
| 6,063,080 A | 5/2000 | Nelson et al. | |
| 6,210,409 B1 | 4/2001 | Ellman et al. | |
| 6,217,573 B1 | 4/2001 | Webster | |
| 6,235,022 B1 | 5/2001 | Hallock et al. | |
| 6,251,134 B1 | 6/2001 | Alt | |
| 6,273,876 B1 | 8/2001 | Klima et al. | |
| 6,356,790 B1 | 3/2002 | Maguire et al. | |
| 6,385,472 B1 | 5/2002 | Hall et al. | |
| 6,464,632 B1 | 10/2002 | Taylor et al. | |
| 6,493,590 B1 | 12/2002 | Wessman et al. | |
| 6,604,003 B2 | 8/2003 | Fredricks et al. | |
| 6,611,699 B2 | 8/2003 | Messing | |
| 6,662,034 B2 | 12/2003 | Segner et al. | |

| | | |
|---|---|---|
| 6,780,183 B2 | 8/2004 | Jimenez, Jr. et al. |
| 6,921,397 B2 | 7/2005 | Corcoran et al. |
| 6,980,843 B2 | 12/2005 | Eng |
| 7,137,395 B2 | 11/2006 | Fried et al. |
| 7,389,148 B1 * | 6/2008 | Morgan .................. 607/116 |
| 7,815,635 B2 | 10/2010 | Wittkampf et al. |
| 7,824,406 B2 | 11/2010 | Wang et al. |
| 7,857,810 B2 | 12/2010 | Wang et al. |
| 7,873,401 B2 * | 1/2011 | Shachar .................. 600/424 |
| 8,048,072 B2 * | 11/2011 | Verin et al. .................. 606/41 |
| 8,187,267 B2 | 5/2012 | Pappone et al. |
| 2001/0012956 A1 | 8/2001 | Behl et al. |
| 2002/0058866 A1 | 5/2002 | Segner et al. |
| 2002/0103426 A1 | 8/2002 | Segner et al. |
| 2002/0156420 A1 | 10/2002 | Anderson et al. |
| 2003/0088244 A1 | 5/2003 | Swanson et al. |
| 2003/0125730 A1 | 7/2003 | Berube et al. |
| 2004/0015215 A1 | 1/2004 | Fredricks et al. |
| 2004/0153056 A1 | 8/2004 | Muller et al. |
| 2004/0181138 A1 | 9/2004 | Hindricks et al. |
| 2004/0204671 A1 | 10/2004 | Stubbs et al. |
| 2004/0231683 A1 | 11/2004 | Eng et al. |
| 2004/0236350 A1 | 11/2004 | Lewis et al. |
| 2004/0243143 A1 | 12/2004 | Corcoran et al. |
| 2004/0267106 A1 | 12/2004 | Segner et al. |
| 2005/0004563 A1 | 1/2005 | Racz et al. |
| 2005/0049583 A1 | 3/2005 | Swanson |
| 2005/0054989 A1 | 3/2005 | McGuckin, Jr. et al. |
| 2005/0070894 A1 | 3/2005 | McClurken |
| 2005/0096647 A1 | 5/2005 | Steinke et al. |
| 2005/0197633 A1 | 9/2005 | Schwartz et al. |
| 2005/0272975 A1 | 12/2005 | McWeeney et al. |
| 2006/0004353 A1 | 1/2006 | Koyfman et al. |
| 2006/0064123 A1 | 3/2006 | Bonnette et al. |
| 2006/0149192 A1 | 7/2006 | Deniega et al. |
| 2006/0200191 A1 | 9/2006 | Zadno-Azizi |
| 2006/0278246 A1 | 12/2006 | Eng et al. |
| 2006/0287650 A1 | 12/2006 | Cao et al. |
| 2007/0021743 A1 * | 1/2007 | Rioux et al. .................. 606/32 |
| 2007/0060847 A1 | 3/2007 | Leo et al. |
| 2007/0073288 A1 * | 3/2007 | Hall et al. .................. 606/41 |
| 2008/0091193 A1 | 4/2008 | Kauphusman et al. |
| 2008/0161789 A1 | 7/2008 | Thao et al. |
| 2008/0249522 A1 | 10/2008 | Pappone et al. |
| 2008/0275428 A1 | 11/2008 | Tegg et al. |
| 2008/0294158 A1 | 11/2008 | Pappone et al. |
| 2009/0012517 A1 | 1/2009 | de la Rama et al. |
| 2009/0018497 A1 | 1/2009 | Birchard et al. |
| 2010/0004632 A1 | 1/2010 | Wu et al. |
| 2010/0174177 A1 | 7/2010 | Wu |
| 2011/0118582 A1 | 5/2011 | de la Rama et al. |
| 2012/0265130 A1 | 10/2012 | de la Rama et al. |

FOREIGN PATENT DOCUMENTS

| | | | |
|---|---|---|---|
| GB | EP0109178 A2 * | 10/1983 | .............. A61N 1/04 |
| WO | WO-96/034652 | 11/1996 | |
| WO | 2005048858 A1 | 6/2005 | |
| WO | WO-2005/094661 | 10/2005 | |

OTHER PUBLICATIONS

"International Search Report and Written Opinion", PCT/US2011/027907 May 13, 2011.

"International Search Report and Written Opinion of the International Searching Authority", PCT/US2008/069248 Jan. 15, 2009.

"Supplementary European Search Report", EP 08827495.6-2305 May 29, 2010.

International Search Report and Written Opinion of the International Searching Authority, PCT/US2010/049836, Nov. 15, 2010.

\* cited by examiner

*Primary Examiner* — Linda Dvorak

*Assistant Examiner* — Brian M Antiskay

(74) *Attorney, Agent, or Firm* — Armstrong Teasdale LLP

(57) ABSTRACT

A catheter includes a flexible tubing having a proximal end and a distal end. The catheter also includes an electrode assembly attached to the distal end of the flexible tubing and including a first magnet therein. The electrode assembly including an electrically conductive tip electrode and an electrically nonconductive coupler which is connected between the tip electrode and the distal end of the flexible tubing. The electrically conductive tip electrode comprises a hollow elongated tip electrode including a sidewall provided with one or more elongated gaps extending through the sidewall. The one or more elongated gaps providing flexibility in the sidewall for bending movement of the tip electrode relative to a longitudinal axis of the catheter body. The first magnet is responsive to an external magnetic field to selectively position and guide the electrode assembly within a body of a patient.

27 Claims, 21 Drawing Sheets

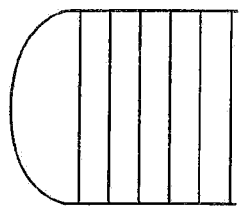
FIG. 13A
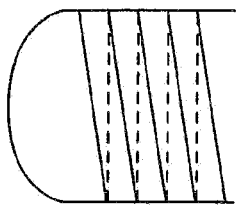
FIG. 13B
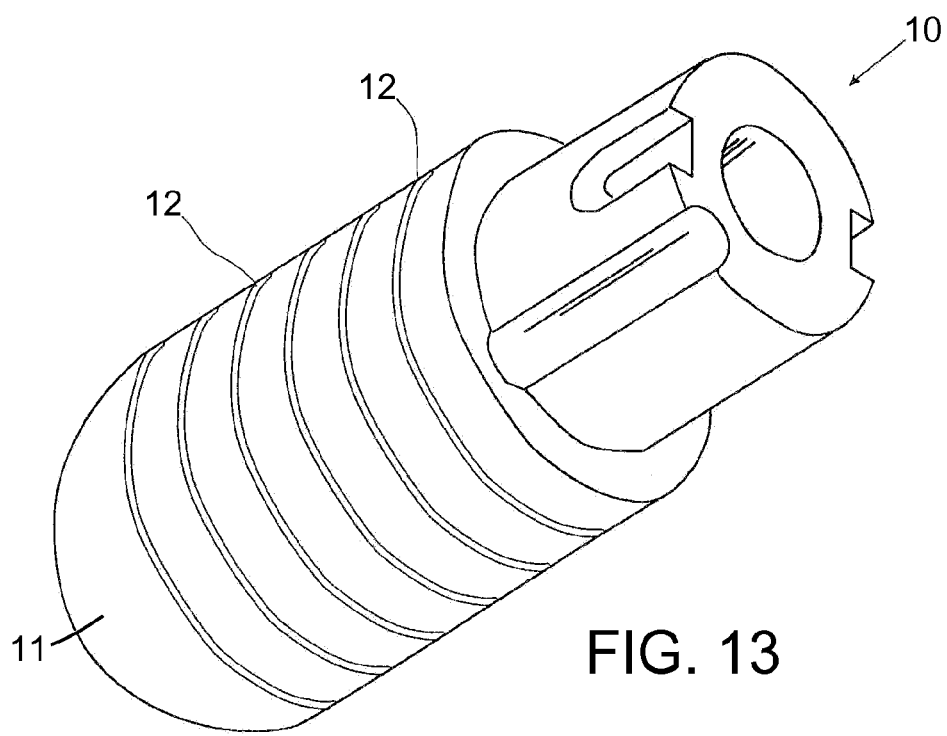
FIG. 13
FIG. 13C
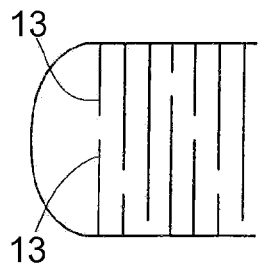

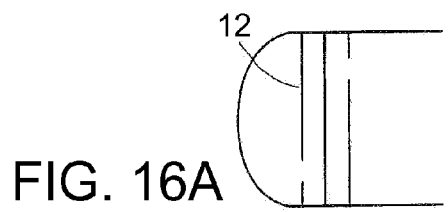
FIG. 16A
FIG. 16B
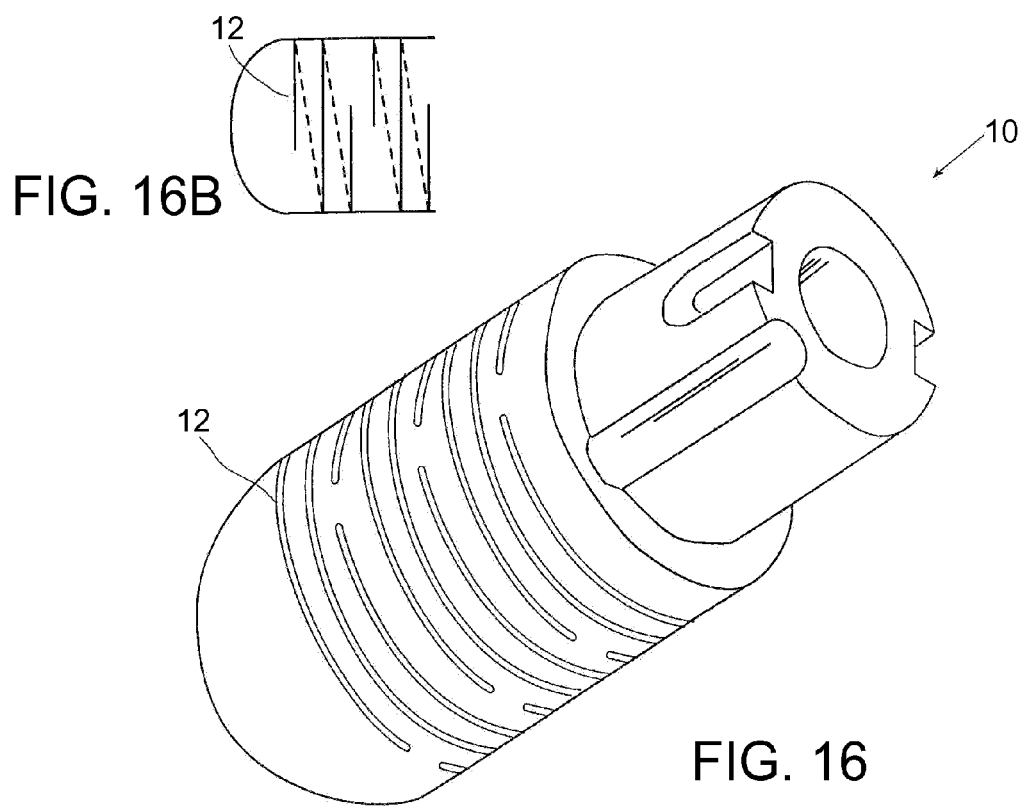
FIG. 16

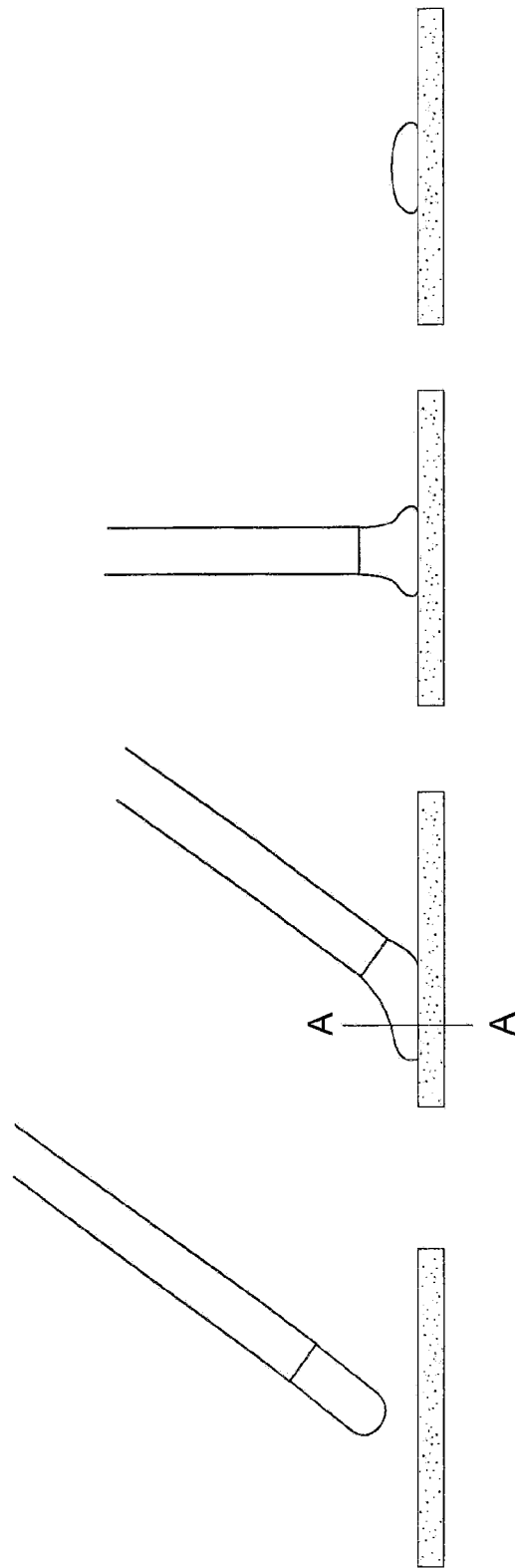

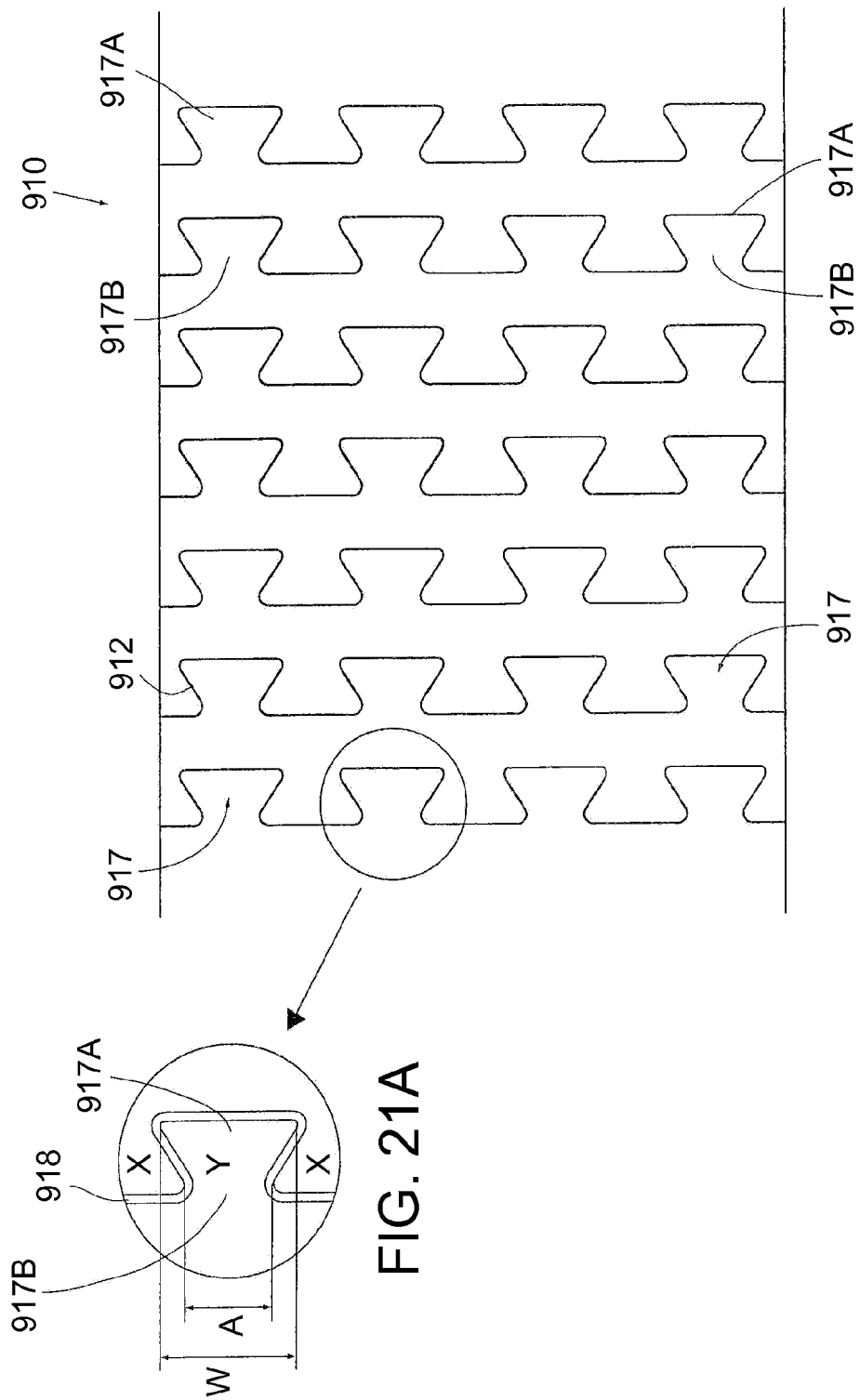

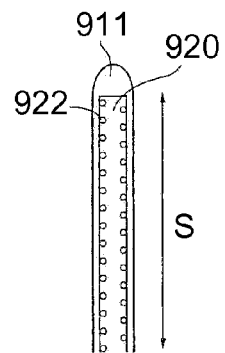
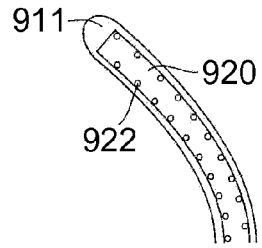
FIG. 26A  FIG. 26B
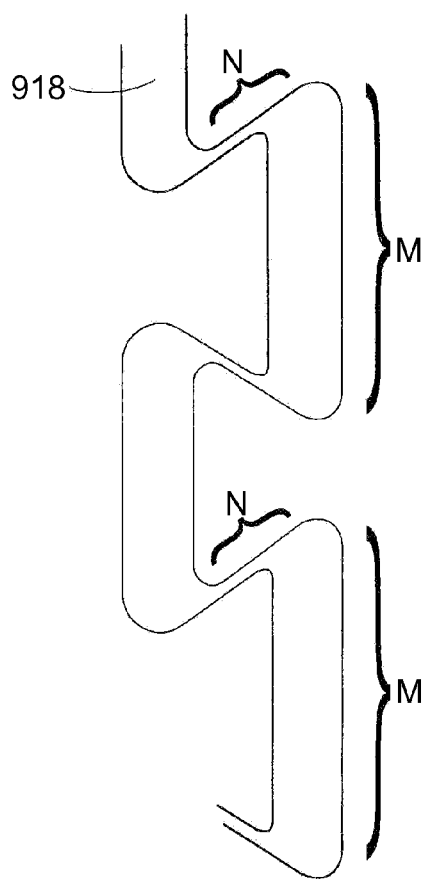
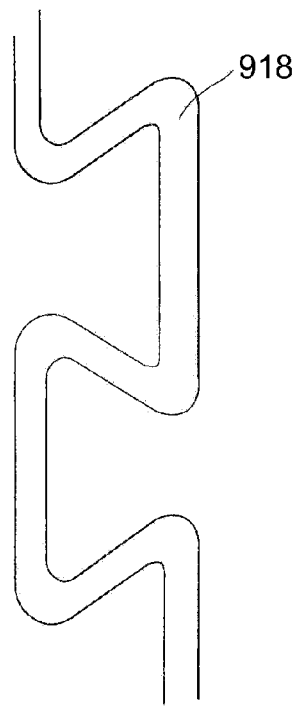
FIG. 27A  FIG. 27B

MAGNETICALLY GUIDED CATHETER WITH FLEXIBLE TIP

CROSS REFERENCE TO RELATED APPLICATIONS

This application is a national stage filing based upon international application no. PCT/US2008/069248, filed 3 Jul. 2008 (the '248 application), which claims the benefit of U.S. provisional application No. 60/947,791, filed 3 Jul. 2007 (the '791 application). This application is also a continuation of U.S. application Ser. No. 11/853,759, filed 11 Sep. 2007 (the '759 application), which claims the benefit of U.S. provisional application No. 60/939,799, filed 23 May 2007 (the '799 application). The '248 application, the '791 application, the '759 application, and the '799 application are all hereby incorporated as though fully set forth herein.

BACKGROUND OF THE INVENTION

This invention relates generally to medical instruments, and, more specifically, to a navigable catheter device positionable within a body of a patient using an externally applied magnetic field.

Catheters are flexible, tubular devices that are widely used by physicians performing medical procedures to gain access into interior regions of the body. Careful and precise positioning of the catheters within the body is important to successfully completing such medical procedures. This is particularly so when catheters are used to produce emissions of energy within the body during tissue ablation procedures. Conventionally, positioning of such catheters was accomplished with mechanically steerable devices. More recently, magnetically navigable catheter devices have been developed that may be navigated with an externally applied magnetic field. Such catheter devices can be complex in their construction, and therefore are difficult to manufacture and relatively expensive to produce.

Magnetic stereotactic systems have been developed that are particularly advantageous for positioning of catheters, as well as other devices, into areas of the body that were previously inaccessible. Such systems utilize computer controlled superconducting coils to generate specific magnetic fields or gradients to move a catheter that is provided with magnetic components responsive to such magnetic fields. The magnetic fields and gradients are generated to precisely control the position of the catheter within the patient's body. Once correctly positioned, physicians may operate the catheter, for example, to ablate tissue to clear a passage in the body. Specifically, such stereotactic systems monitor the position of a tip of the catheter in response to the applied magnetic fields of the superconducting coils, and using well established feedback and control algorithms the catheter tip may be guided to and positioned in a desired location within the patient's body.

The magnetic response of the catheter can be a limitation on the precise control of a catheter when used with such magnetic guidance systems. Improvements in catheters utilized with magnetic guidance and control systems, such as stereotactic systems, are desired. Specifically, a low cost, yet high performance magnetically guided catheter is desirable.

BRIEF DESCRIPTION OF THE INVENTION

In various embodiments, magnetic guided catheters are disclosed that are manufacturable at relatively low cost while providing high performance while used with, for example, magnetic stereotactic systems.

In one embodiment, a catheter is provided that includes a flexible tubing having a proximal end and a distal end. The catheter also includes an electrode assembly attached to the distal end of the flexible tubing and including a first magnet therein. The electrode assembly including an electrically conductive tip electrode and an electrically nonconductive coupler which is connected between the tip electrode and the distal end of the flexible tubing. The electrically conductive tip electrode comprises a hollow elongated tip electrode including a sidewall provided with one or more elongated gaps extending through the sidewall. The one or more elongated gaps providing flexibility in the sidewall for bending movement of the tip electrode relative to a longitudinal axis of the catheter body. The first magnet is responsive to an external magnetic field to selectively position and guide the electrode assembly within a body of a patient.

In another embodiment, a catheter is provided that includes a tubing having a proximal end and a distal end. The catheter also includes an electrode assembly attached to the distal end of the tubing and including a magnet therein. The electrode assembly including an electrically conductive tip electrode and an electrically nonconductive coupler which is connected between the tip electrode and the distal end of the tubing. The electrically conductive tip electrode comprises a cylindrical hollow body including a wall having a pattern of one or more elongated gaps in the wall through a thickness of the wall. The elongated gaps provide axial freedom of movement and allow the electrode to shorten its axial length when a force is applied to the electrode. The magnet is responsive to an external magnetic field to selectively position and guide the electrode assembly within a body of a patient.

In a further embodiment, a catheter is provided that includes a tubing having a proximal end and a distal end. The catheter also includes an electrode assembly attached to the distal end of the tubing and including a magnet therein. The electrode assembly includes an electrically conductive tip electrode. The electrically conductive tip electrode includes a hollow electrode body defined by a sidewall extending along a longitudinal axis. The sidewall is provided with a pattern including one or more elongated gaps through a thickness of the wall. The elongated gaps imparting flexibility to the sidewall to adopt different operating configurations relative to the longitudinal axis. The magnet is responsive to an external magnetic field to selectively position and guide the electrode assembly within a body of a patient.

BRIEF DESCRIPTION OF THE DRAWINGS

FIG. 13 is a perspective view of an exemplary embodiment of a flexible tip electrode for a catheter.

FIGS. 13A-13C illustrate alternative embodiments of the flexible tip electrode shown in FIG. 13.

FIG. 16 is a perspective view of another embodiment of a flexible tip electrode.

FIGS. 16A-16B are alternative embodiments of the flexible tip electrode shown in FIG. 16.

FIGS. 20A-20C illustrate further embodiments of catheters having flexible electrode tips in use.

FIG. 20D is a cross-sectional view of a portion of FIG. 20B taken along line A-A.

FIG. 20E schematically illustrates an altered cross sectional shape for the electrode tip shown in FIG. 20C.

FIG. 21 is a side elevational view of a portion of another embodiment of flexible tip electrode.

FIG. 21A is a magnified view of a portion of FIG. 21.

FIG. 26A is a longitudinal cross-sectional view of a further embodiment of a tip electrode.

FIG. 26B is a longitudinal cross-sectional view of still another embodiment of a tip electrode.

FIG. 27A is an illustrative view showing an exemplary electrode gap for forming a flexible tip electrode.

FIG. 27B is an illustrative view of another electrode gap for forming a flexible electrode tip.

DETAILED DESCRIPTION OF THE INVENTION

Many specific details of certain embodiments of the invention are set forth in the following description in order to provide a thorough understanding of such embodiments. One skilled in the art, however, will understand that the present invention may have additional embodiments, or that the present invention may be practiced without several of the details described in the following description.

Figure 1:
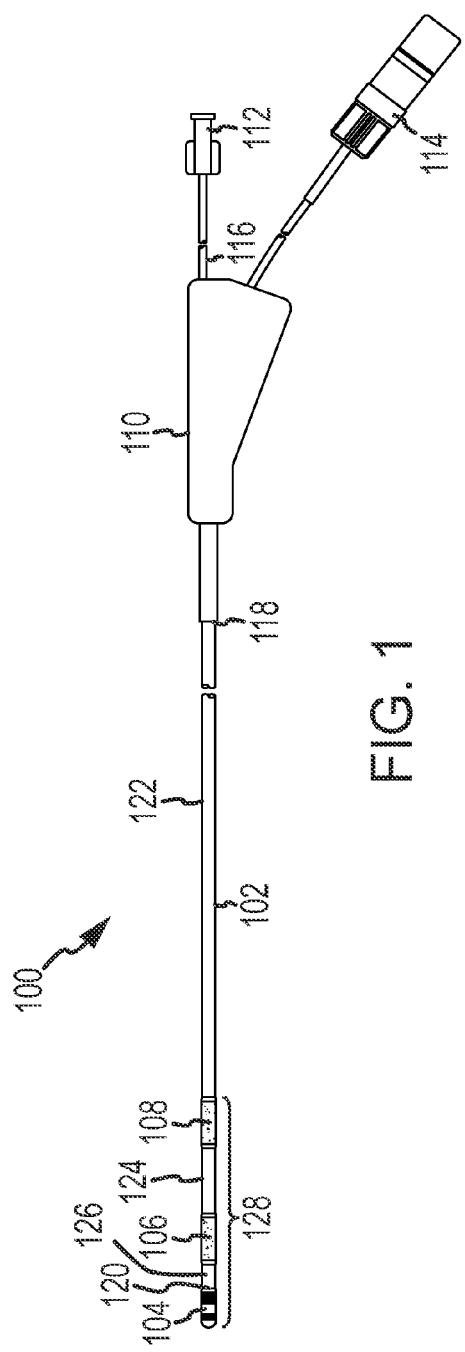
FIG. 1 illustrates a first exemplary magnetic guided catheter.

FIG. 1 illustrates a first exemplary non-steerable, single-use magnetically guided catheter 100 generally including a flexible outer tube, or tubing, 102, a tip assembly 104, positioning magnets 106 and 108 separately provided from and spaced from tip assembly 104, a Y connector 110, a luer device 112, and an electrical connector 114. Luer device 112 is used to open or close a flow path so that fluid is passed through Y-connector 110 and tubing 102 to tip assembly 104 for irrigation purposes. Electrical connector 114 establishes electrical connection with a power source (not shown) that operates electrodes of tip assembly 104 to perform, for example, ablation procedures, mapping or pacing procedures, or to perform other aspects of a medical procedure.

Although it will become evident that aspects of exemplary catheter 100 are applicable to a variety of medical procedures and end uses, the invention will be described principally in the context of a specific example of a magnetically guided catheter. Specifically, catheter 100, as shown in FIG. 1, is believed to be particularly advantageous as an ablation catheter for creating endocardial lesions during cardiac ablation procedures to treat arrhythmias, and also for cardiac electrophysiological mapping and delivering diagnostic pacing stimuli. However, the invention and the appended claims are not intended to be limited to any specific example, including but not limited to specific examples or embodiments described herein, except when explicitly defined as such in the appended claims.

Y-connector 110 separates an inner tube 116 from electrical lead wires (not shown) extending between tip assembly 104 and electrical connector 114. More specifically, tube 116 and the lead wires forward of Y-connector 110 pass internally through outer tube 102, while aft of Y-connector 110, inner tube 116 and leads for the lead wires are exposed and separated for connection to a fluid source (not shown) and the power source, respectively. In one embodiment, electrical connector 114 is a known connector configured to engage the power source or a power supply with, for example, a plug-in connection. One suitable electrical connector is a 14 pin REDEL® plastic connector commercially available from LEMO of Rohnert Park, Calif., although other connectors from various manufacturers may likewise be utilized.

Outer tube 102 includes a proximal end 118 coupled to Y-connector 110, a distal end 120 coupled to tip assembly 104, and an axial length extending between proximal end 118 and distal end 120. In one embodiment, flexible tubing 102 is fabricated according to known processes, such as extrusion processes, from any suitable tubing material known in the art of medical instruments, such as engineered nylon resins and plastics, including but not limited to PEBAX® tubing of Ato Fina Chemicals, France.

In an exemplary embodiment tubing 102 is fabricated from a first tubing material defining a first portion 122 of tubing 102 between Y connector 110 and magnet 108, a second tubing material defining a second portion 124 of tubing 102 between magnet 106 and magnet 108, and a third tubing material defining a third portion 126 of tubing 102 extending between magnet 106 and tip assembly 104. In an exemplary embodiment, first portion 122, second portion 124 and/or third portion 126 are fabricated from different materials and grades of materials for enhanced performance of tubing 102 in use of catheter assembly 100. Tubing 102, by virtue of portions 122, 124, and 126 having varying flexible properties, is sometimes referred to as a multi-flexible tube.

For example, in one embodiment, the first material defining first portion 122 of tubing 102 is a comparatively rigid and kink resistant braided material. First portion 122 is formed with different portions of braided material, semi-soft material, and soft material fused to one another so that first portion 122 becomes increasingly flexible along the axial length as first portion 122 approaches magnet 108. The second material defining second portion 124 of tubing 102, and the third material defining third portion 126 of tubing 102 is a soft and flexible material having approximately equal flexible properties. In the illustrated embodiment, each of tubing portions 122, 124, and 126 between tip assembly 104 and magnets 106 and 108 share a common outside diameter of, for example, 7 French, although in other embodiments, tubing portions 122, 124 and 126 have varied diameters.

As shown in FIG. 1, first portion 122 extends for a majority of the axial length of tubing 102 between the proximal end 18 and distal end 120. Second portion 124 of tubing 102 extends for a shorter length than the length of first portion 122, and the third portion 126 of the tubing extends for a length that is shorter than the length of second portion 124. By way of example only, in a specific embodiment first portion 122 extends for an axial length of about 126.3 cm, second portion 124 extends for an axial length of about 2.2 cm, and third portion 126 extends for an axial length of about 0.8 cm, although other relative lengths of the tube portions may likewise be employed in other embodiments. The different relative lengths of tube portions 122, 124 and 126, as well as the different flexible properties of tube portions 122, 124 and 126, allow tip assembly 104 to be more precisely positioned within a patient's body, while also avoiding problems of kinks and excessive deflection of tubing 102 along the majority of its length during use and handling.

As another consequence of tubing sections 124 and 126 having an unequal length, magnet 106 is spaced a first distance from tip assembly 104, and magnet 108 is spaced a second, greater distance from magnet 106 since tubing portion 124 is longer than tubing portion 126. Due to the spacing of magnets 106 and 108 relative to one another and also to tip assembly 104, which as explained below also includes a positioning magnet (not shown in FIG. 1), the spacing of magnets 106 and 108 permits positioning adjustment of tip assembly 104 in response to variations in an externally applied magnetic field that may otherwise not be possible, if magnets 106 and 108 were provided in an equal or uniform spaced relation to one another. It is contemplated, however, that in another embodiment tip 104, magnet 106 and magnet 108 are equally spaced from one another.

In operation, a distal end portion 128 of catheter 100 including tip assembly 104 is navigated to a site in the body where a medical procedure, such as an atrial mapping, pacing and/or ablation are to occur. Distal end portion 128 may extend, for example, into a heart chamber of a patient. Once distal end portion 128 is in the heart chamber, a magnetic field is applied to provide an orienting force to distal end portion 128, causing the tip positioning magnet and magnets 106 and 108 to respond to the applied magnetic field and flex tubing portions 124 and 122 to precisely position the tip assembly 104 for performance of the procedure at a specific location.

The magnetic fields used to orient tip assembly 104 are, in one embodiment, generated with a magnetic stereotactic system (not shown). Such stereotactic systems are known and are commercially available from, for example, Stereotaxis of St. Louis, Mo. Such systems may include movable source magnets outside the body of the patient, and operative details of such systems are disclosed in, for example, U.S. Pat. Nos. 6,475,223 and 6,755,816, the disclosures of which are hereby incorporated by reference in their entirety. While catheter 100 is advantageous for use with a stereotactic system, it is contemplated that magnetic fields and gradients to deflect catheter tip assembly 104 may alternatively be generated by other systems and techniques if desired.

Figure 2:
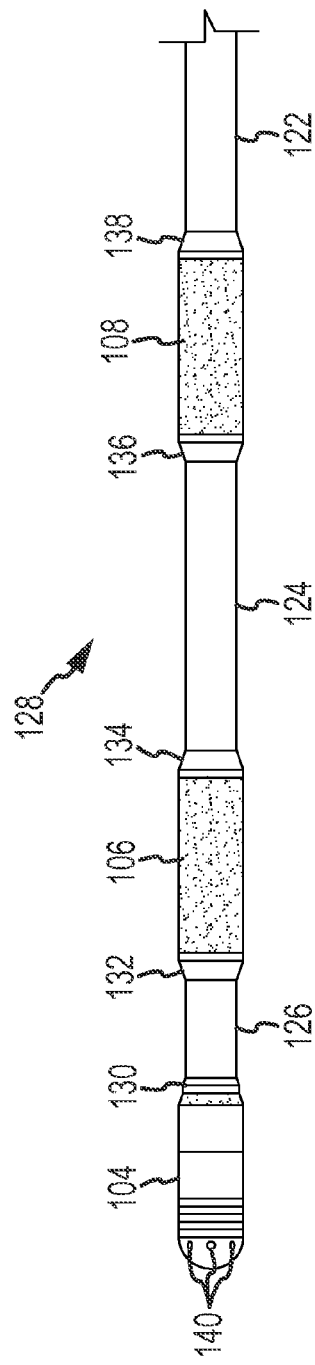
FIG. 2 is a magnified view of a distal end portion of the catheter shown in FIG. 1.

FIG. 2 is a magnified view of distal end portion 128 of catheter 100 shown in FIG. 1. Tip assembly 104 is coupled to a first end 130 of tube portion 126 and magnet 106 is coupled to a second end 132 of tube portion 126. A first end 134 of tube portion 124 is coupled to magnet 106 and a second end 136 of tube portion 124 is coupled to magnet 108. A first end 138 of tube portion 122 is coupled to magnet 108, and a second end (not shown in FIG. 2) of tube portion 122 is coupled to connector 110 (shown in FIG. 1). As shown in FIG. 2, tip assembly 104 includes irrigation ports or openings 140 for passage of fluid from within tubing 102 (shown in FIG. 1) to an exterior of tip assembly 104 when located in the body of a patient.

Figure 3:
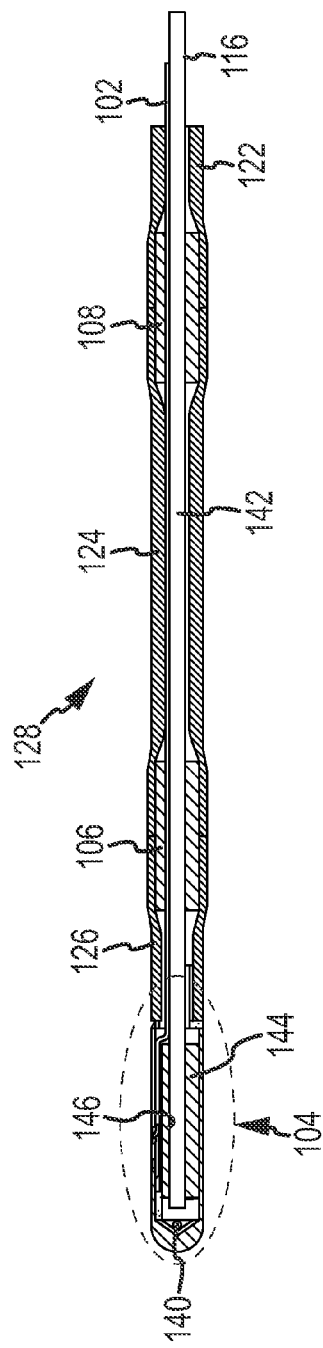
FIG. 3 is a cross sectional view of the distal end portion shown in FIG. 2.

FIG. 3 is a cross sectional view of distal end portion 128 wherein inner tube 116 defines a central lumen 142 extending through each tube portion 122, 124, and 126, and also through central bores formed in magnets 106 and 108. Inner tube 116 has an outer diameter that is smaller than an inner diameter of tubing 102 and its portions 122, 124, and 126 such that space extends between an outer surface of inner tube 116 and an inner surface of tubing 102. In one embodiment, this space is used to accommodate lead wires for electrical components of tip assembly 104.

Tip assembly 104 also includes a positioning magnet 144 having an internal bore 146 passing therethrough. Inner tube 116 passes through central bore 146 in magnet 144. Central lumen 142 is in fluid communication with luer 112 (shown in FIG. 1) on one end and with the irrigation ports 140 extending through tip assembly 104 at the other end. Thus, an irrigation fluid, such as saline, may be injected through distal end portion 128. Inner tube 116 may be, for example, a braided polyimide tube that maintains the flowpath through lumen 142 in all orientations of tip assembly 104, without compromising the flexibility of tubing 102.

Figure 4:
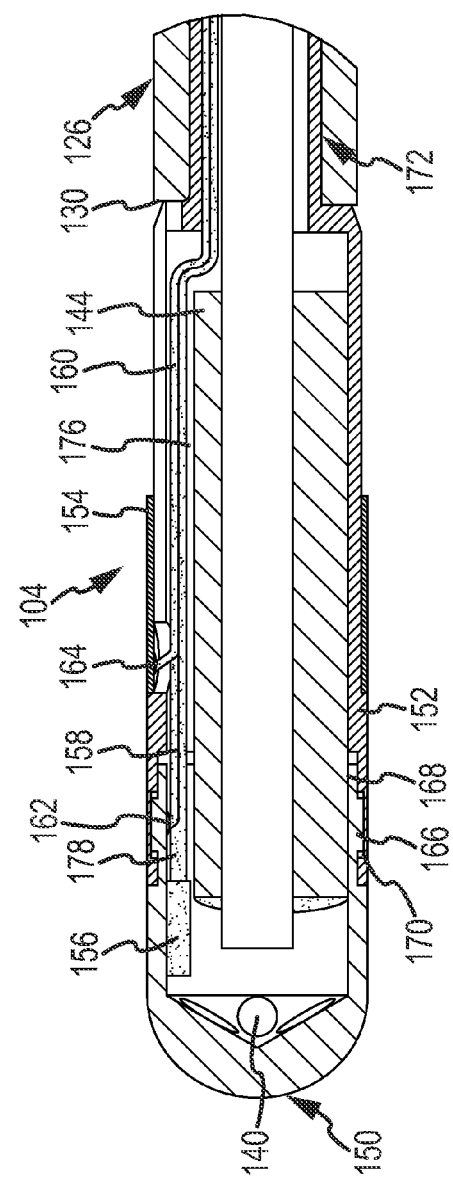
FIG. 4 is a magnified cross sectional view of the electrode tip assembly shown in FIGS. 2 and 3.

FIG. 4 is a magnified cross sectional view of tip assembly 104. In an exemplary embodiment tip assembly 104 includes a tip electrode 150, a coupler 152, a band electrode 154, positioning magnet 144, and a temperature sensor 156. Lead wires 158, 160 extend to tip electrode 150, and to band electrode 154 on first respective ends 162, 164 thereof, and to connector 114 (shown in FIG. 1) on second ends (not shown) so that electrodes 150 and 154 and may be energized by a power source (not shown).

In the exemplary embodiment, tip electrode 150 may be, for example an 8 Fr hemispherical-shaped tip electrode that is 2 mm in length. In other embodiments, other sizes of tip electrodes may be utilized, including but not limited to 4 mm or 8 mm tip electrodes. Tip electrode 150 is formed with a plurality of openings that form irrigation ports 140 for saline irrigation. In the exemplary embodiment, tip electrode 150 is fabricated from 90% platinum and 10% iridium, or other materials known in the art such that tip electrode 150 is viewable under fluoroscopic exposure. While formed as an integral unit, tip electrode 150 may include multiple electrode elements, such as ring electrodes for electrophysiological mapping purposes, spaced from one another by dielectric materials as is known in the art.

Coupler 152 is a generally cylindrical, electrically nonconductive member. It is typically made of a polymer such as PEEK™, which is relatively rigid compared to rubber and has a limited amount of flexibility and resiliency to form a snap-fit connection, for example. Tip electrode 150 is formed with an annular projection 166 on its outer surface that engages a groove 168 within a first end 170 of coupler 152 to form a snap-fit, interlocking connection. Alternatively, any mating configuration of tip assembly 104 and coupler 152 may be used. Coupler 152 includes a second end 172 that is fitted within first end 130 of tube portion 126. Additionally, or alternatively thereto, first end 170 of coupler 152 is adhered to tip electrode 150. Second end 172 of coupler 152 is adhered to the inner diameter of tube portion 126. Heat shrink techniques or adhesives may also be utilized to permanently attach coupler 152 to tube portion 126 and/or tip electrode 150. The positioning magnet 144 is disposed in a cavity which is formed at least partially inside the coupler 152 and which may be formed partially inside the coupler 152 and partially inside the tip electrode 150. The coupler 152 houses the positioning magnet 144 in the tip assembly 104 and supports the optional band electrode 154, is more rigid than the flexible tubing 102, and provides a convenient and reliable connection between the tip electrode 150 and the third portion 126 of the flexible tubing 102.

Band electrode 154 is, in one embodiment, an 8 Fr ring-shaped band electrode that is for example, 2 mm in length, and spaced from tip electrode 150 by a predetermined distance of 2 mm. Band electrode 154 is, in one embodiment, fabricated from the same material as or a different material from tip electrode 150 and is attached to an outer surface of coupler 152.

In one embodiment, tip positioning magnet 144 is a generally cylindrical shaped permanent magnet fabricated from a known magnetic material, such as neodymium-iron boron-45 (NdFeB-45). Alternatively, magnet 144 is formed from other materials and may have shapes different from the elongated cylindrical shape illustrated.

As shown in FIG. 4, magnet 144 includes an axially extending recess, or groove, 176 formed into an exterior of magnet 144. Lead wires 158, 160, and a lead wire 178 for temperature sensor 158 pass through recess 176 in a space defined by recess 176 and an inner surface of coupler 152. Temperature sensor 158 is, in one embodiment, a thermocouple type temperature sensor, and lead wires 158, 160, and 178 are, for example, 38 AWG wires having quad polyimide insulation.

Tip assembly 104 is particularly suited for ablation procedures wherein electrodes 150 and 154 are energized to deliver radio frequency waves at the site of an abnormal electrical pathway in the body. Radiofrequency (RF) energy may therefore be applied to biological tissue in proximity to tip assembly 104. Ablation procedures are typically used, for example, within the interior chambers of the heart to thermally ablate cardiac tissue. Electrodes 150 and 154 may additionally be operated to record intracardiac signals and to provide pacing signals.

Figure 5:
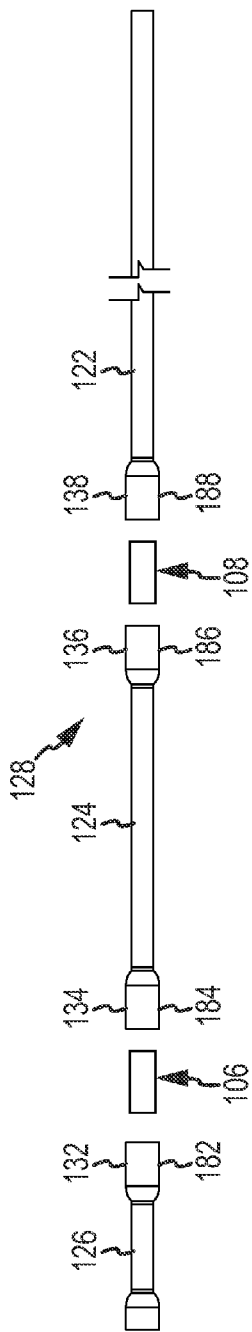
FIG. 5 is an exploded view of the distal end portion shown in FIG. 2 of the catheter shown in FIG. 1.

FIG. 5 is an exploded view of catheter distal end portion 128 (shown in FIG. 1). Magnets 106 and 108 are each permanent magnets formed from, for example, neodymium-iron boron-45 (NdFeB-45) into an elongated tubular shape.

As shown in FIG. 5, second end 132 of tube portion 126, first and second ends 134, 136 of tube portion 124, and first end 138 of tube portion 122 are formed into outwardly flared sockets 182, 184, 186 and 188. Magnet 106 is received in socket 182 of tube second end 132 and socket 184 of tube portion first end 134. Magnet 108 is received in socket 186 of tube portion second end 136 and socket 188 of tube portion first end 138. In the exemplary embodiment, sockets 182, 184, 186, and 188 are formed with a flaring tool and extend, for example, an axial length of about 2.5 mm. Sockets 182, 184, 186, and 188 are, in the exemplary embodiment, adhered to magnets 106 and 108, respectively, and heat shrunk to fuse sockets 182 and 184 to magnet 106 and sockets 186 and 188 to magnet 108. In another embodiment, sockets 182, 184, 186, and 188 are maintained in position with a friction fit. In the exemplary embodiment, adjacent tube ends 132 and 134 as well as adjacent tube ends 136 and 138 contact each other and, in a particular embodiment, are fused to each other.

Tube portions 122, 124, and 126 have an outer diameter, at locations other than sockets 182, 184, 186, and 188, that is smaller than the outer diameter of tube portions 122, 124, and 126 at the location of sockets 182, 184, 186, and 188. In one embodiment, the outer diameter of magnets 106 and 108 is the same as, or larger than, the outer diameter of tube portions 122, 124, and 126 at locations other than sockets 182, 184, 186, and 188. The larger diameter magnets are able to provide an enhanced response for positioning of catheter 100 (shown in FIG. 1) with externally applied magnetic fields.

Figure 6:
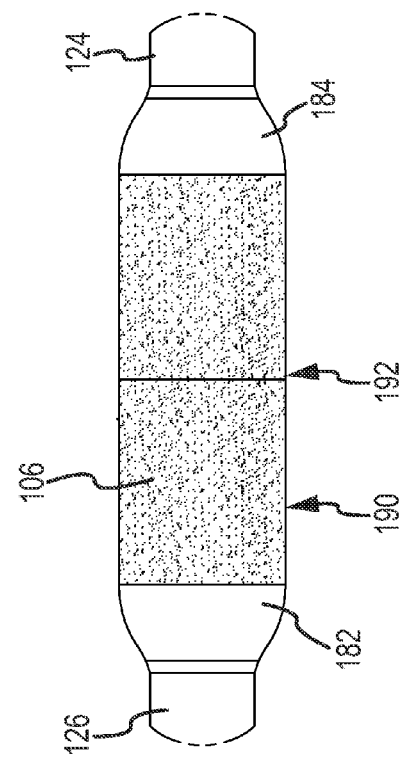
FIG. 6 illustrates an enlarged view of an alternate connecting structure for the attachment of the tube portions to the magnets.

FIG. 6 illustrates an enlarged view of an alternate connecting structure for the attachment of tube portions 126 and 124 to magnet 106. As shown in FIG. 6, a sleeve member 190 extends over sockets 182 and 184 and forms a smooth outer surface for a transition 192 from tube portion 126 over magnet 106 to tube portion 124. Sheath 190 is, in one embodiment, fabricated from a thin tube of a polyimide material, or any other material that provides a low coefficient of friction.

Although only three tube portions 122, 124, and 126 and two magnets 106 and 108 spaced from tip assembly 104 are shown in FIGS. 1-6, it should be understood that fewer than, or more than three tube portions and two magnets could be used without departing from the spirit of the hereinabove described catheter.

FIGS. 7 through 11 illustrate a second exemplary embodiment of a magnetically guided catheter 200 that is similar in many aspects to catheter 100 described above. Like components and features of catheter 100 are indicated with like reference numbers in FIGS. 7 through 11. Unlike catheter 100, catheter 200 includes a distal end portion 202 that is different from tip assembly 104 described above. Distal end portion 202 includes magnets 204 and 206 (instead of magnets 106 and 108), rounded tip electrode 208, and tip element 210.

Figure 8:
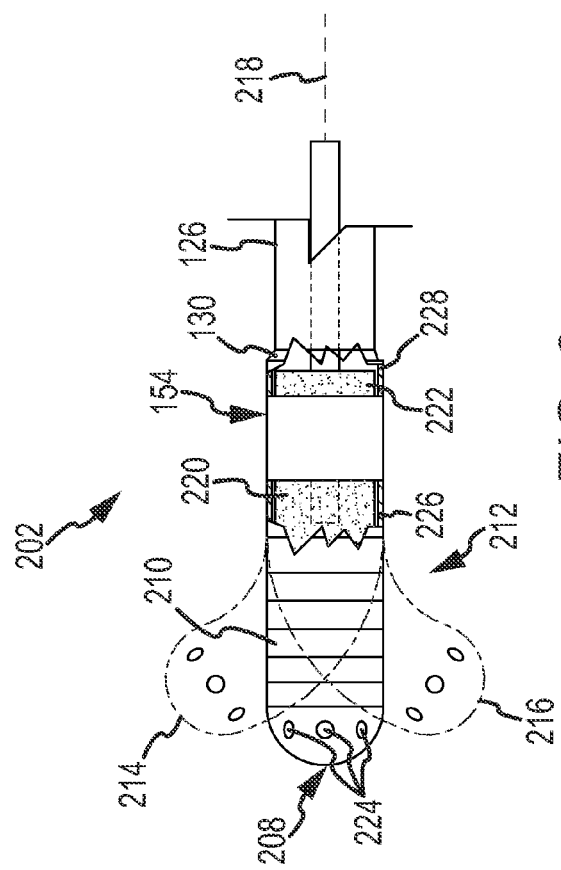
FIG. 8 illustrates an electrode assembly for the catheter shown in FIG. 7.

FIG. 8 illustrates distal end portion 202 including a tip assembly 212 that includes rounded tip electrode 208 and tip element 210. Tip element 210 is a flexible member that allows tip assembly 212 to flex, bend or deflect along its axial length to, for example, different operating positions 214 and 216 (shown in phantom in FIG. 8) in addition to the in-line configuration shown in solid lines in FIG. 8 wherein the tip is straight and generally linear along a longitudinal axis 218.

Tip assembly 212 also includes a coupler 220 that joins tip element 210 to tube portion 126, a band electrode 154, and a positioning magnet 222 provided internal to tip assembly 212. In the exemplary embodiment, tip electrode 208 may be, for example an 8 Fr hemispherical-shaped tip electrode that is 2 mm in length. In other embodiments, other sizes of tip electrodes may be utilized, including but not limited to 4 mm or 8 mm tip electrodes. Tip electrode 208 is formed with a plurality of openings that form irrigation ports 224 for saline irrigation. In the exemplary embodiment, tip electrode 208 is fabricated from 90% platinum and 10% iridium, or other materials known in the art such that tip electrode 208 is viewable under fluoroscopic exposure. While formed as an integral unit, tip electrode 150 may include multiple electrode elements, such as ring electrodes for electrophysiological mapping purposes, spaced from one another by dielectric materials as is known in the art.

Coupler 220 is a generally cylindrical, electrically nonconductive member. It is typically made of a polymer such as PEEK™, which is relatively rigid compared to rubber and has a limited amount of flexibility and resiliency to form a snap-fit connection, for example. The coupler 220 is connected at a first end 226 to tip element 210 and at a second end 228 to first end 130 of tube portion 126. Coupler 220 is, in one embodiment, engaged to tip element 210 with a snap-fit, interlocking engagement similar to the coupler 152 in FIG. 4. Additionally, or alternatively thereto, coupler 220 is adhered to tip element 210. In addition, coupler 220 is adhered to an inner section of tube portion 126. Heat shrink techniques may also be utilized to permanently attach coupler 220 to tube portion 126 and/or tip element 210. The positioning magnet 222 is disposed in a cavity which is formed at least partially inside the coupler 220 and which may be formed partially inside the coupler 220 and partially inside the tip element 210. The coupler 220 houses the positioning magnet 222 in the tip assembly 212 and supports the optional band electrode 154, is more rigid than the flexible tubing 102, and provides a convenient and reliable connection between the tip element 210 and the third portion 126 of the flexible tubing 102.

Band electrode 154 is, in one embodiment, an 8 Fr ring-shaped band electrode that is for example, 2 mm in length, and spaced from tip electrode 208 by a predetermined distance of 2 mm. Band electrode 154 is, in one embodiment, fabricated from the same material as or a different material from tip electrode 150 and is attached to an outer surface of coupler 220.

In one embodiment, tip positioning magnet 222 is a generally cylindrical shaped permanent magnet fabricated from a known magnetic material, such as neodymium-iron boron-45 (NdFeB-45). Alternatively, magnet 222 is formed from other materials and may have shapes different from the elongated cylindrical shape illustrated.

Figure 9:
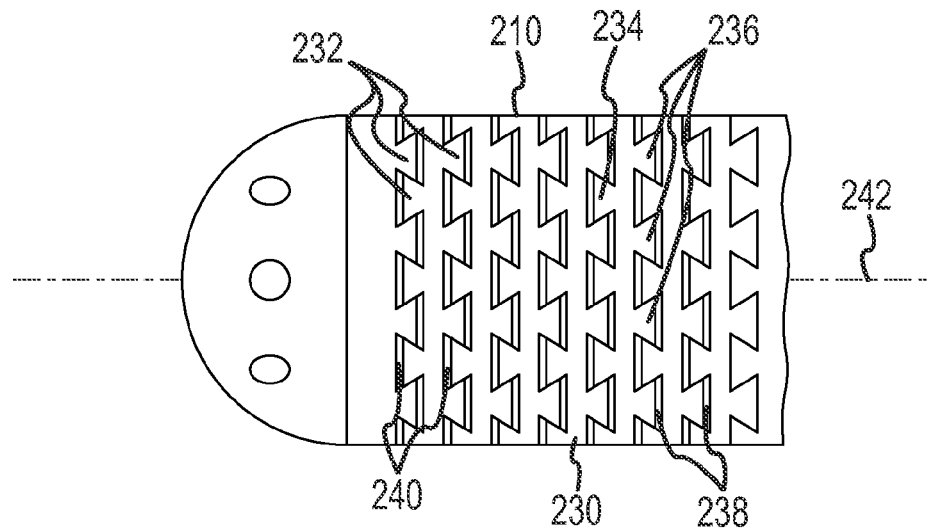
FIG. 9 is a magnified assembly view of a portion of the tip assembly shown in FIG. 8.

FIG. 9 illustrates exemplary tip element 210 in further detail. In the exemplary embodiment, tip element 210 is comprised of a single member that is formed into a helix, or spiral, and extends from tip electrode 208 to coupler 220. Tip element 210 includes a helically shaped body 230 having alternately spaced projections 232 extending away from body 230 in opposite directions from one another along the length of the helix. That is, a first set of projections 234 extends distally, i.e., towards tip electrode 208, and a second set of projections 236 extends proximally, i.e., away from tip electrode 208. The first set of projections 234 are staggered or offset from the second set of projections 236 such that the first set of projections 234 are offset from, and positioned between, the second set of projections 236.

Recesses 238 extend between projections 232 and are complementary in shape to an outer contour of projections 232, but inversely shaped from projections 232. In the illustrated embodiment, projections 232, and recesses 238, are trapezoidal in shape, although it is contemplated that other shapes could likewise be utilized in alternative embodiments.

Tip element 210 is fabricated such that projections 232 from one section of body 230 extend into, and are captured within, recesses 238 from an adjacent section of body 230 to form an interlocking arrangement. Due to projections 232 being complementary in shape to recesses 238 and thus defining sockets or compartments for projections 232, projections 232 are movable only a defined distance within recesses 238. In particular, and as shown in FIG. 9, tip element 210 is positionable to create a space or gap 240 between leading edges of projections 232 and inner edges of recesses 238. Projections 232 and recesses 238 of tip element 210 extend completely along the length of body 230 and, in one embodiment, are uniformly spaced and sized around a perimeter of body 230. Alternatively, projections 232 and recesses 238 may be differently sized and/or spaced around the perimeter of body 230.

As a consequence of gaps 240, and also the complementary shapes of projections 232 and recesses 238, projections 232 are provided a freedom of movement within recesses 254 without being able to be removed therefrom. Accordingly, sections of tip element 210 can move toward and away from each other a defined distance to decrease and increase, respectively, gaps 240. It is thus possible for sections of tip element 210 to move relative to one another in multiple ways. For example, tip element 210 may be compressed so that all of gaps 240 are closed, or nearly closed, to reduce the longitudinal length of tip assembly 202 by the cumulative dimensions of gaps 240 along a longitudinal axis 242. Additionally, sections of tip element 210 may exhibit cascaded or sequential movement along longitudinal axis 242 wherein some gaps 240 are closed along longitudinal axis 242 while other gaps remain open, either partially or fully. This allows gaps 240 between any adjacent sections of tip element 210 to be opened or closed in an uneven or non-uniform manner. As such, gaps 240 on one side of tip assembly 202 may be closed while gaps 240 on the other side of tip assembly 202 may be opened. The result of this configuration is that tip assembly 202 curves in the direction of the closed gaps 240 and away from the direction of the opened gaps 240. It can be appreciated that movement in vertical and horizontal planes may simultaneously occur due to the interlocking construction of tip element 210 to flex and deflect the tip assembly 202 to a practically unlimited number of positions. Tip assembly 202 may deflect in the manner described due to, for example, impact forces on an outer surface of tip assembly 202 in use, and may also, in whole or in part, be the result of the magnetic response of positioning magnet 222 (shown in FIG. 8) and magnets 204 and 206 (shown in FIG. 7).

In an exemplary embodiment, tip element 210 is laser cut from a material suitable for surgical use, such as an electrically conductive, non-corrosive material. In one exemplary embodiment, the material is platinum. In another exemplary embodiment, the material is stainless steel. Projections 232 and recesses 238 of tip element 210 are, in the exemplary embodiment, laser cut out of a cylindrical piece of material. It should be evident that as the number of helices increases in tip element 210, the flexing capability also increases. In addition, as the pitch of the helix decreases, the ability of tip element 210 to move relative to itself increases. The flexibility may further be adjusted by providing different numbers and shapes of projections and recesses to produce tip assemblies that flex to varying degrees to meet different objectives. The combination of the multi-flexing tubing previously described and independent flexing of the tip assembly 212 is particularly advantageous for certain applications. For example, RF energy may be more specifically targeted to desired tissue areas for ablation procedures when tip element 212 is flexed than when it is not flexed, and provides a physician with additional positioning capability over conventional catheter devices.

In an alternative embodiment, tip assembly includes a plurality of adjacent rings that extend along longitudinal axis 242. Each ring has a distal side and a proximal side and each side includes alternating projections and recesses. This structure provides for flexibility in a manner that is similar to the exemplary embodiment described above. In such a configuration, the rings are constructed substantially identically to each other.

Tip assembly 212 is particularly suited for ablation procedures wherein electrode 208 is energized to deliver radio frequency waves at the site of an abnormal electrical pathway in the body. Radiofrequency (RF) energy may therefore be applied to biological tissue in proximity to tip assembly 212. Ablation procedures are typically used, for example, within the interior chambers of the heart to thermally ablate cardiac tissue. Electrode 208 may additionally be operated to record intracardiac signals and to provide pacing signals. It should be noted that tip assembly 212 is also suited for recording of intracardiac signals and to provide pacing signals. While formed as an integral unit, tip electrode 208 may include multiple electrode elements, such as ring electrodes for electrophysiological mapping purposes, spaced from one another by dielectric materials as is known in the art.

Figure 7:
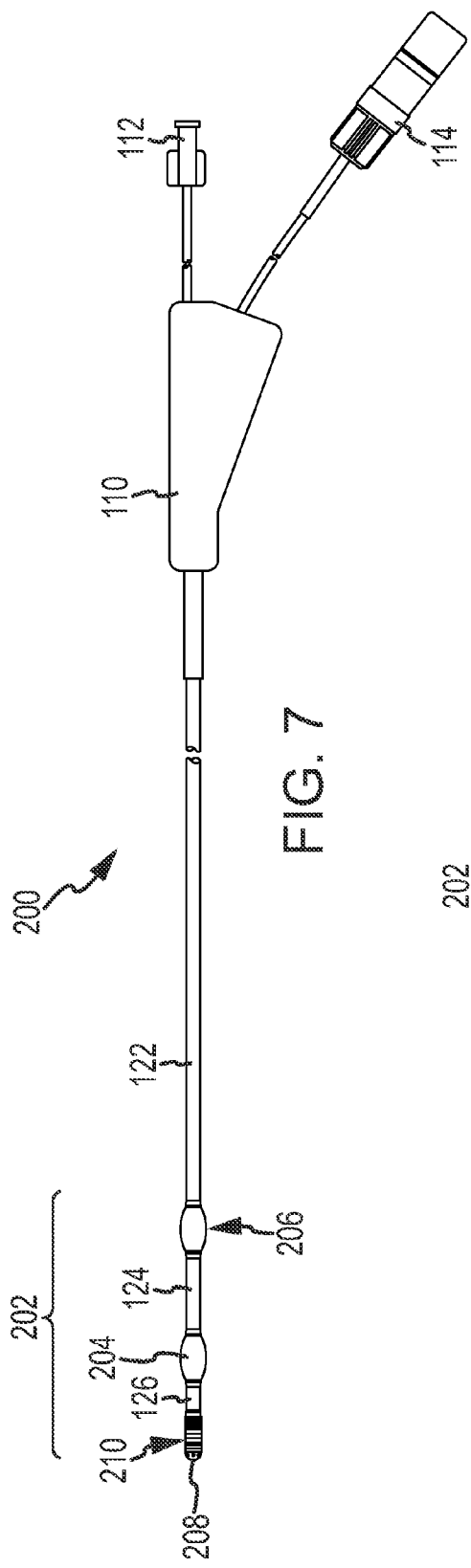
FIG. 7 illustrates a second exemplary embodiment of a magnetically guide catheter.
Figure 10:
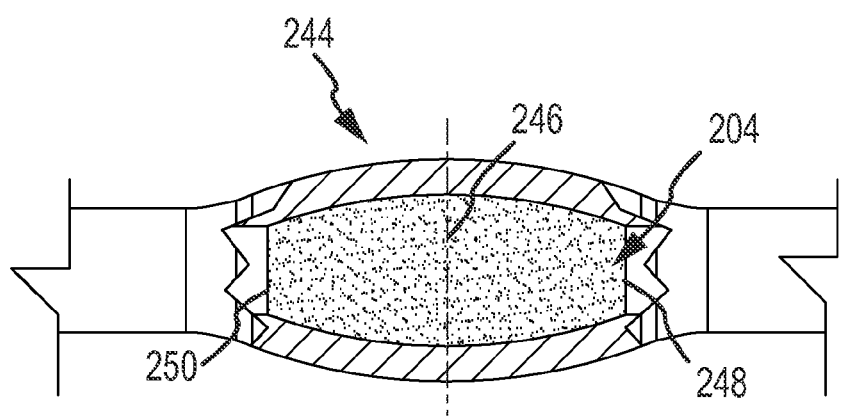
FIG. 10 illustrates a magnet assembly for the catheter shown in FIG. 7.

FIG. 10 illustrates a magnet assembly 244 for catheter 200 (shown in FIG. 7). Unlike magnets 106 and 108 (shown in FIG. 1) that are cylindrical in shape and have a constant outer diameter, magnet 204 is outwardly flared and has a generally ellipsoidal contour. That is, the outer diameter of magnet 204 is largest at an axial midpoint 246 and decreases from midpoint 246 to opposing ends 248, 250 of magnet 204, providing magnet 204 with a curved profile along an axial length of magnet 204.

In one embodiment, magnet 204 is encapsulated in sockets formed into adjacent tube portions as described above. Alternatively, magnet 204 is encapsulated in a sleeve that extends from the tube portions to cover magnet 204. Similarly to magnets 106 and 108, magnet 204 includes a central bore through which a tube passes. Magnet 204 is formed from, for example, neodymium-iron boron-45 (NdFeB-45) into the illustrated shape or an alternative shape. It should be understood that magnet 206 (shown in FIG. 7) may be formed in the same shape as or a different shape from magnet 204.

Figure 11:
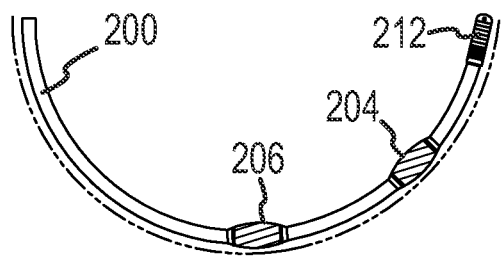
FIG. 11 illustrates a distal portion of the catheter shown in FIG. 7 in an operating position.

FIG. 11 illustrates a distal portion of catheter 200 in an exemplary operating position that shows the deflection of tip assembly 212 and magnets 204 and 206. By applying magnetic fields to magnets 204 and 206, and also positioning magnet 222 (shown in FIG. 7), the distal portion of catheter 200 may be precisely positioned at a specific location within the patient's body. The magnetic fields may be generated and controlled by, for example, a magnetic stereotactic system (not shown).

Figure 12:
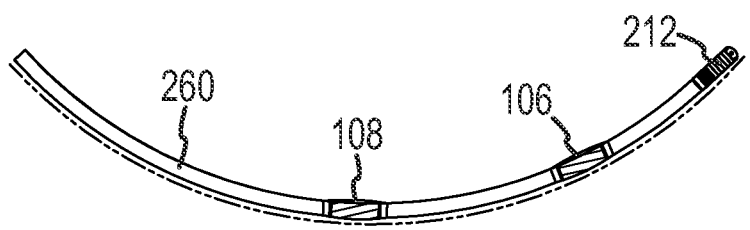
FIG. 12 illustrates a third exemplary embodiment of a distal portion of a magnetically guided catheter including a flexible tip and cylindrical magnets.

FIG. 12 illustrates a distal portion of an alternative catheter, such as a catheter 260. Catheter 260 shows a distal portion of catheter 260 in an exemplary operating position in which the deflection is caused by tip assembly 212 and magnets 106 and 108. By applying magnetic fields to magnets 106 and 108, and also positioning magnet 222 (shown in FIG. 7), the distal portion of catheter 260 may be precisely positioned at a specific location within the patient's body. The magnetic fields may be generated and controlled by, for example, a magnetic stereotactic system (not shown).

The external positioning magnets of the catheters 100, 200, and 260 are believed to provide manufacturing benefits, and also performance benefits, in relation to conventional, and more complicated, catheter constructions for use with stereotactic systems. Larger positioning magnets are provided for increased magnetic response and performance, and tubing is used that is generally smaller in internal diameter than the magnets, thereby resulting in material savings in comparison to known catheters having larger tubing to accommodate the magnets. In addition, increased flexibility is provided. Sockets in the tubes encapsulate the external positioning magnets in a very manufacturable and generally low cost construction. The external positioning magnets that are separately provided from the electrode tips also reduce a complexity and parts count in the tip assembly relative to other known catheter tips providing comparable functionality.

One example of a flexible tip electrode is shown in FIG. 9 above. Additional embodiments and configurations are illustrated in FIGS. 13-29.

Referring now to FIG. 13, an exemplary tip electrode 10 includes a hollow and generally cylindrical body having a dome tip 11 and a cylindrical sidewall. The sidewall may include a series of annular or ring-like surface channels or grooves 12 cut or otherwise formed into the sidewall. Grooves 12 define elongated areas of decreased wall thickness and decreased cross-sectional area of the sidewall, and hence the areas of the wall occupied by elongated grooves 12 are structurally weaker and less rigid than areas of the sidewall where the grooves are not present, imparting flexible properties to the electrode wall. As used herein, an elongated groove preferably has a length that is at least about 3 times the width of the groove, more preferably at least about 5 times, and most preferably at least about 10 times.

As shown in FIG. 13, elongated grooves 12 are disposed about tip electrode 10 and extend generally parallel to one another. Each annular groove 12 extends in a plane that is generally perpendicular to a longitudinal axis of tip 11. The respective grooves 12 may be spaced equidistant from each other along a longitudinal length of the tip electrode. Each annular groove 12 may form a continuous 360 degree unending loop (as illustrated in FIG. 13A) that is circular. Alternatively, all or part of the series of ring grooves may extend in a non-circular and a non-planar helical configuration (as shown in FIG. 13B) completing more than one 360 degree loop or turn on the surface of the electrode sidewall, with the helical ring grooves having discrete end points.

In another embodiment, the electrode may include some annular rings extending in a plane that do not form a continuous unending loop, but rather grooves forming loops having two terminal ends 13 (as depicted in FIG. 13C) that are spaced apart from one another. A further embodiment may include a combination of continuous and non-continuous, planar and non-planar groove configurations.

In alternative embodiments, elongated openings extending completely through the thickness of the sidewall of the electrode may be provided in lieu of elongated surface channels or grooves. As used herein, an elongated opening preferably has a length that is at least about 3 times the width of the opening, more preferably at least about 5 times, and most preferably at least about 10 times.

Elongated openings extending completely through the electrode sidewall will generally impart more flexibility, or less rigidity, in the sidewall than will elongated surface channel grooves. In the embodiment shown in FIG. 13A, however, if each complete loop is completely cut through the sidewall, some type of additional supporting structure is required to connect the severed-pieces together. For example, a biasing element such as an inner coil may be provided within the lumen, such as in the embodiments of FIGS. 26A and 26B to be described further below.

Figures 14, 14A, 14B, 14C, 14D:
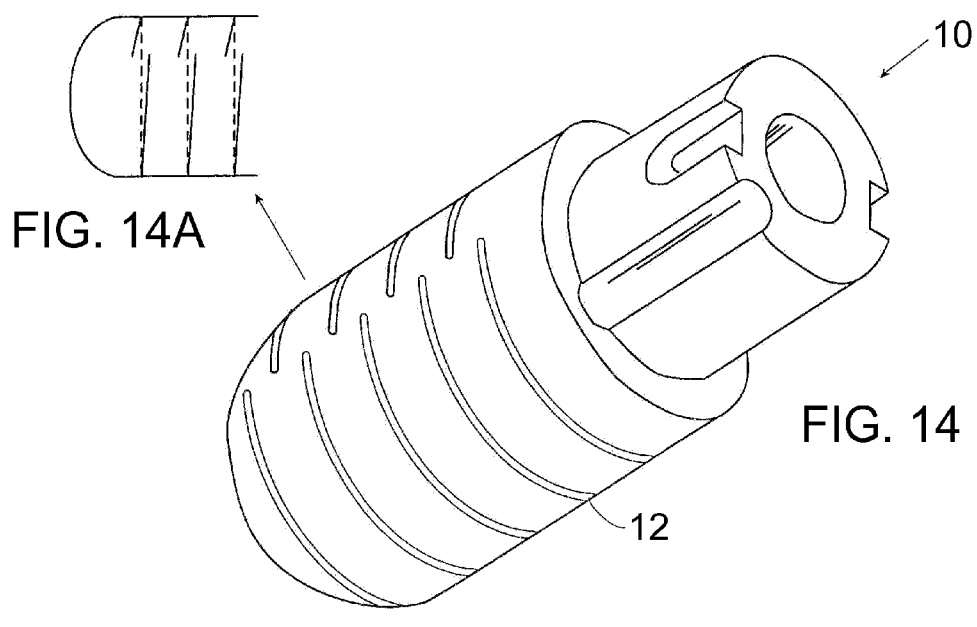
FIG. 14 is a perspective view of another embodiment of a flexible tip electrode for a catheter.
FIGS. 14A-14D illustrate alternative embodiments of the flexible tip electrode shown in FIG. 14.

Referring now to FIG. 14, elongated ring-like, annular grooves 12 may be spaced further apart than in the embodiment shown in FIG. 13. Also, in the embodiment of FIG. 14, each ring-like, annular groove does not form a continuous, 360 degree loop on the electrode sidewall, and terminal ends of each respective groove are slightly offset or staggered relative to one another to maintain some degree of desired rigidity in the electrode sidewall. As shown in FIGS. 14A through 14C, the elongated grooves may have a circumferential length chosen so that terminal ends 13 of adjacent grooves extend past one another for a specified distance in an interleaved or dovetail arrangement on the electrode sidewall. It is contemplated that in other embodiments a combination of continuous ring-like grooves, such as those shown in FIG. 13, and non-continuous grooves such as those shown in FIG. 14 may be utilized.

FIG. 14D illustrates another embodiment where offset elongated ring-like grooves 12 extend in respective planes spaced along a longitudinal axis of the tip, but the ring-like grooves extend only partly around the cylindrical sidewall of the electrode. In the example shown in FIG. 14D, the elongated grooves 12 extend as staggered half loops extending across about 180 degrees of the cylindrical circumference of the electrode wall. Many other relative positions of half loops are also contemplated. In other embodiments, some or all of elongated grooves 12 may extend across more or less than 180 degrees of the cylindrical circumference of the electrode sidewall.

Figure 15A:
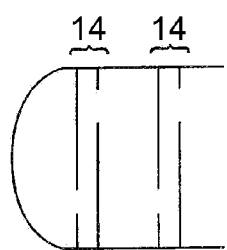
FIG. 15A is a side view of the tip electrode shown in FIG. 15.
Figure 15:
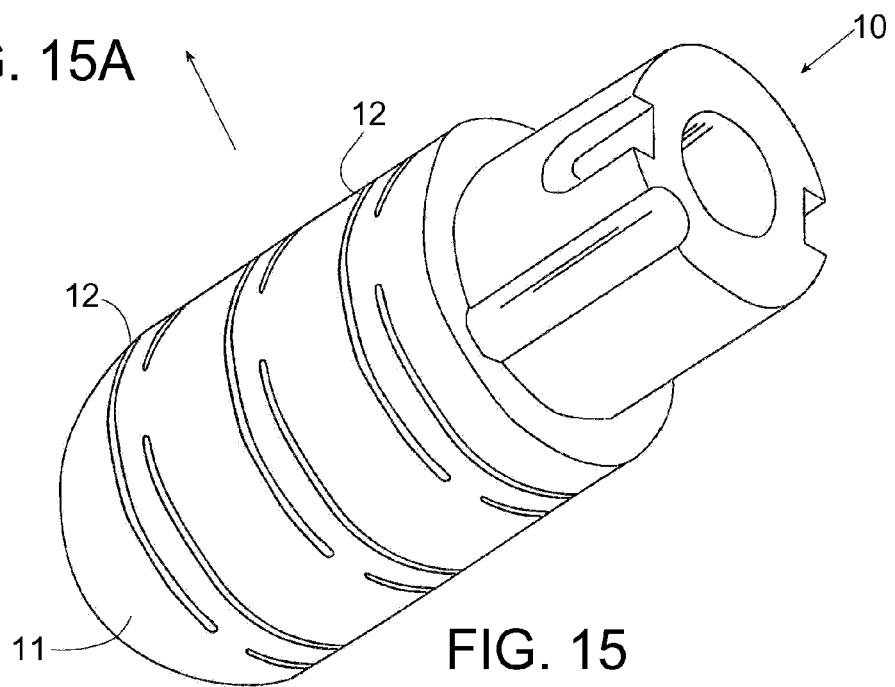
FIG. 15 is a perspective view of another embodiment of a flexible tip electrode for a catheter.

FIGS. 15 and 15A illustrate a tip electrode wherein three sets of elongated grooves 12 are provided, with each set 14 including two non-continuous ring-like loops. Spacing between sets 14 is generally greater than spacing between the two ring-like loops in each set.

FIG. 16 illustrates still further embodiments of a tip electrode. In the embodiment shown in FIG. 16A, the elongated ring-like grooves form non-continuous loops on the outer surface of the electrode sidewall, with each groove having terminal ends that do not connect with each other. In the embodiment illustrated in FIG. 16B, a series of elongated helical grooves 12 are provided that each extend for a number of turns on the surface of the electrode wall.

Figure 17:
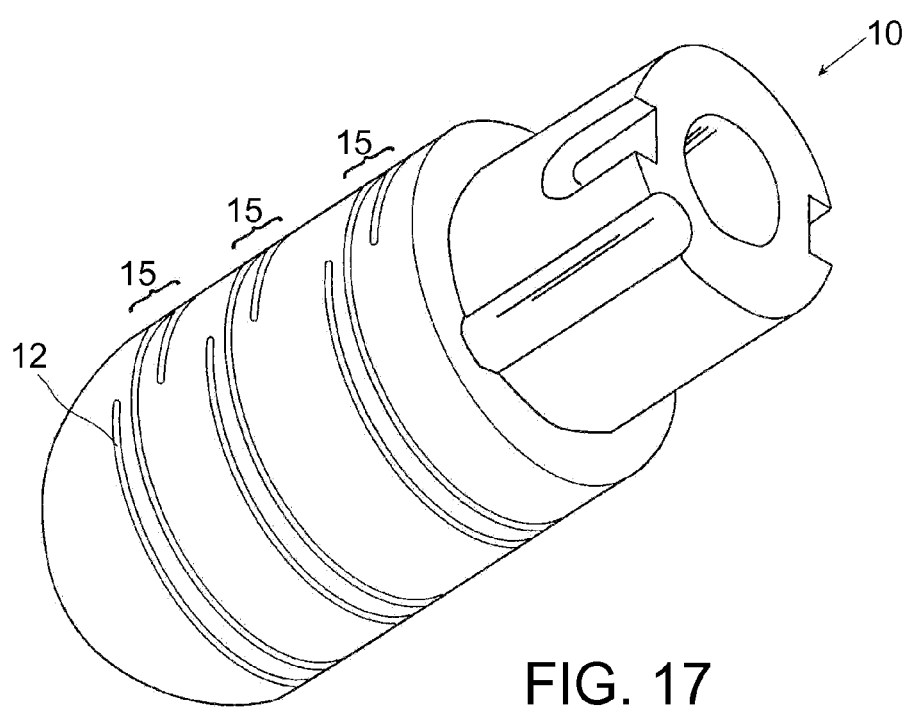
FIG. 17 is a perspective view of another embodiment of a flexible tip electrode for a catheter.

FIG. 17 illustrates another catheter tip including three sets of elongated grooves 12. Each set 15 is shown to include a helical groove extending more than one 360 revolution or turn on the electrode sidewall.

Figure 18:
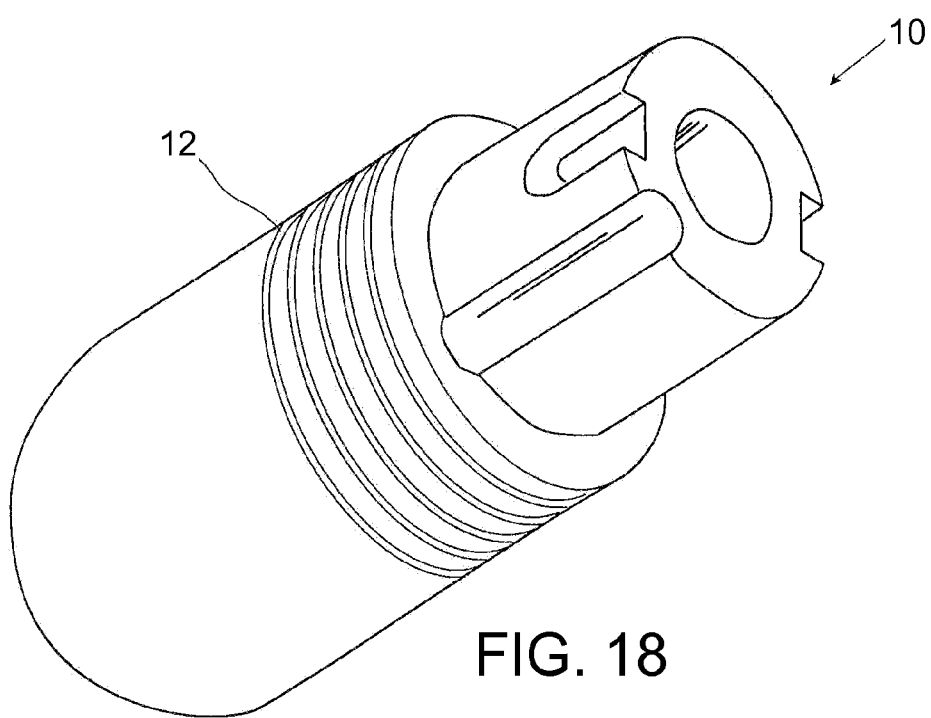
FIG. 18 is a perspective view of another embodiment of a flexible tip electrode for a catheter.

FIG. 18 illustrates yet another contemplated embodiment where a series of elongated, ring-like grooves 12 are disposed generally equidistant from each other only along a proximal section of tip electrode 10. Each ring-like groove 12 may or may not form a continuous loop or a complete turn on the electrode sidewall. A combination of continuous loops and non-continuous loops are possible. By providing elongated grooves 12 in the proximal end of the electrode tip, but not the distal end, a desired rigidity in the distal portion of tip electrode 10 may be provided, while affording some flexibility to the proximal portion of the tip.

Figure 19C:
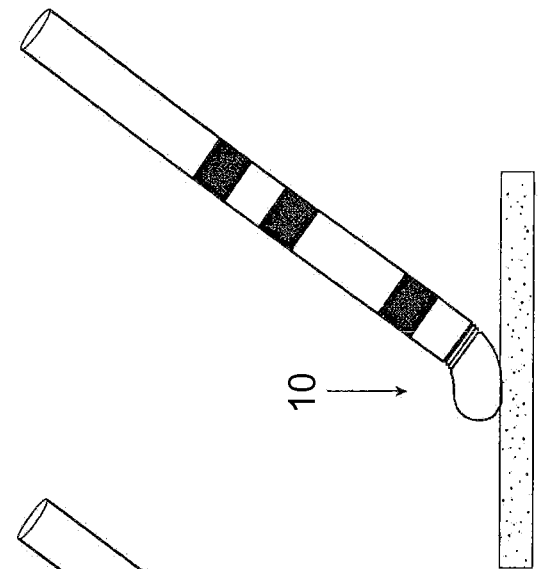
FIGS. 19A-19C illustrate embodiments of catheters having flexible electrode tips in use.
Figure 19B:
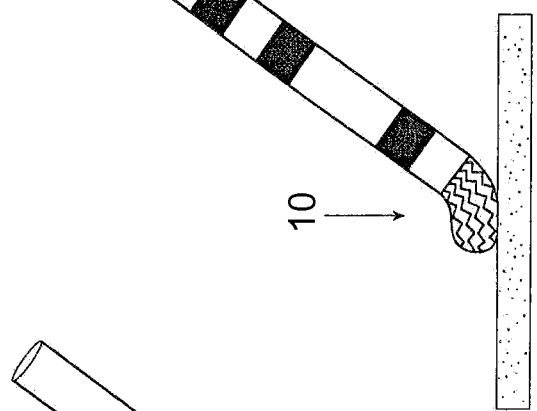
Figure 19A:
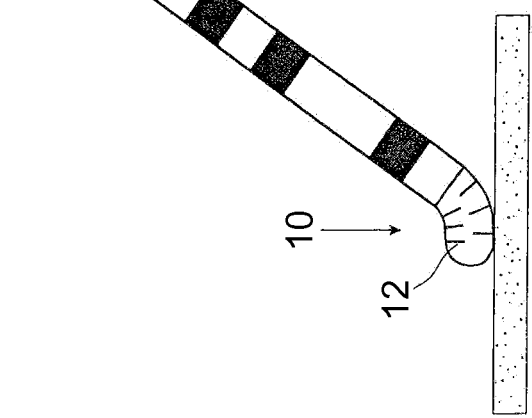

FIGS. 19A through 19C illustrate catheters including embodiments of flexible tip electrodes in use to map or ablate tissue surfaces. One aspect of the flexible tips allows and facilitates effective dragging of the flexible tip electrode 10 across a smooth tissue surface to create a linear lesion. This is possible because, as FIGS. 19A through 19C depict, the flexible tip electrode 10 may deform and/or flex when it is dragged across a tissue surface. The flexible and deformable properties of the flexible tips results in greater electrode-to-tissue surface area than would otherwise be possible with a rigid tip electrode.

In FIG. 19A, the tip electrode includes an elongated cut pattern 12 that is similar to the embodiment depicted in FIG. 14D including relatively parallel rings or loops, but extending completely through the thickness of the electrode wall to impart additional flexibility in comparison to the grooved embodiment of FIG. 14D. In FIG. 19B, a tip electrode with an elongated zigzag cutting pattern allows even greater flexibility than the pattern of FIG. 19A. In FIG. 19C, however, the catheter tip electrode includes elongated grooves only at the neck region where the electrode is attached to the catheter (similar to the embodiment of FIG. 18), allowing some degree of flexibility in a more rigid tip electrode.

FIGS. 20A through 20E illustrate embodiments of the catheters having flexible tip electrodes that may advantageously deform, apart from simple bending along the longitudinal axis of the catheter body as shown in FIG. 19, to create greater electrode-to-tissue surface area. In FIG. 20A, a catheter including a flexible tip electrode is ready to make contact with a tissue surface. When the electrode makes contact with the tissue surface in FIG. 20B, the tip electrode may deform. For example, a cross sectional area of the tip along line A-A in FIG. 20B may become oval in shape as shown in FIG. 20D. Such an electrode may not only flex along a longitudinal axis, but may also expand laterally when subjected to an applied force. When an angle between the tissue surface and a longitudinal axis of the catheter body gets closer to a 90 degree angle as shown in FIG. 20C, the flexible tip may deform and shorten due to downward pressure against the tissue surface. FIG. 20E, for example, schematically illustrates a cross section of the tip electrode in FIG. 20C at a location parallel to the tissue surface. The electrode-to-tissue surface area, represented by the circle in FIG. 20E is expandable outwardly in a direction of arrows 16 as the catheter is pressed further towards the tissue surface. One contemplated embodiment that has deformable properties as shown in FIGS. 29A through 20E is the tip electrode with an elongated zigzag cut pattern as shown in FIG. 19B.

Referring now to FIG. 21, an exemplary embodiment of flexible tip electrode 910 has an elongated cutting pattern in the electrode sidewall that outlines alternating interlocking blocks 917. In the illustrated embodiment, contemplated blocks 917 are disposed on both sides of an elongated gap 918 created by the cutting pattern. Each block has a head 917A and a neck 917B, and the head 917A is wider than the neck 917B in each block. In the illustrated interlocking pattern, a first head, represented by "Y" in FIG. 21A of the block 917, which has a neck 917B situated on one side of gap 918, is disposed between second and third heads represented by "X" in FIG. 21A. The second and third heads X each have necks situated on the other side of elongated gap 918 and opposing the head Y. The blocks X and Y are interlocked because the wider head portion of one block 917 is locked between the narrower neck portions of the two adjacent blocks 917. For example, the second and third heads X in FIG. 21A are separated by a shortest distance A in FIG. 21A, and distance A is shorter than a width W of the head Y, thereby restricting relative movement of two adjacent loops away from each other and preventing the blocks from separating.

Contemplated patterns of elongated openings can also be described by focusing on the structures of the electrode wall, instead of focusing on the shape of gap 918. For example, in FIG. 22, a contemplated electrode wall includes a stem member 919 that may helically extend about a longitudinal axis of the electrode forming a series of stem loops (see FIG. 21), and wherein member 919 includes a plurality of protruding blocks 917 peripherally disposed on both sides of the stem member 919. Each block 917 transversely extends in a lateral direction indicated by arrow T in FIG. 22 toward an adjacent stem loop in the electrode wall shown in FIG. 21. Each adjacent stem loop includes blocks 917 that are staggered from blocks 917 in immediately adjacent stem loops, resulting in an interlocking block pattern. Contemplated blocks for the stem member can have various shapes. For example, at least some of blocks 917 may have a shape of an upside down triangle as illustrated, where one angle of the triangle represents the neck region. Alternatively, blocks with rounded bulbous shape such as ones shown in FIG. 23 may alternatively be utilized. Contemplated heads of the bulbous shapes are wider than their corresponding necks, facilitating an interlocking block pattern.

Figure 22:
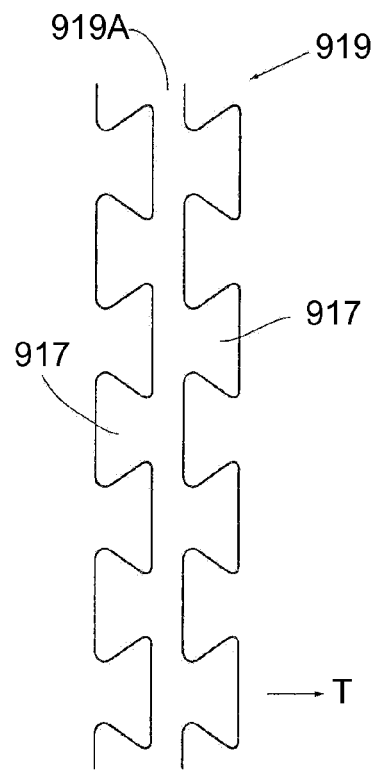
FIG. 22 is a side elevational view of a section of the electrode tip shown in FIG. 21.
Figure 23:
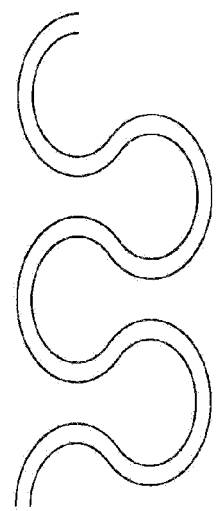
FIG. 23 is a view of an alternative section of an electrode tip.
Figure 24A:
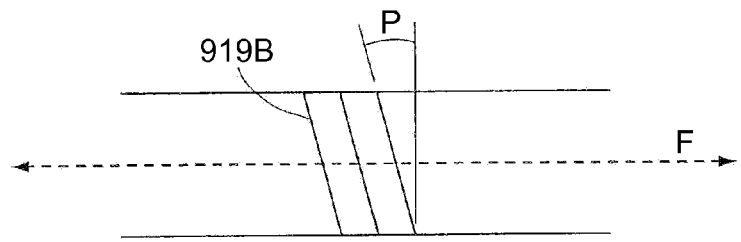
FIG. 24A is schematic illustration of a section of a tip electrode.
Figure 24B:
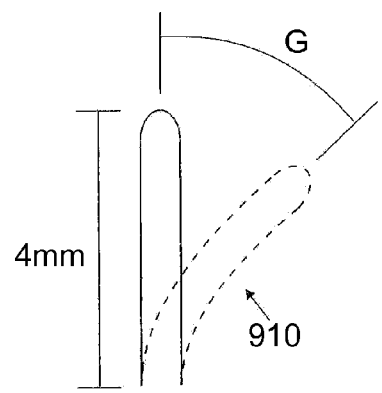
FIG. 24B is a side elevational view of a flexible tip electrode showing a degree of flexing.

The stem members of FIGS. 22 and 23, for example, having an axis 919B, may extend in a helix about the longitudinal axis F in FIG. 24A with a pitch P between and including 0.5 to 10 degrees. To describe it in another way, the patterns of elongated gaps 918 extend helically around the longitudinal axis F with a pitch angle, for example, between and including 0.5 to 10 degrees.

The contemplated elongated openings defining gaps 918 between the blocks of the stem members (FIG. 21) improve a flexibility of the electrode, and allow the electrode to flex and bend along the longitudinal length of the electrode and relative to the catheter body to which it is attached. For example, the ability of the electrode to flex allows an approximately 4 mm length of the electrode to bend at an angle G in FIG. 24B that falls, for example, between and including 0.2 degrees to 70 degrees relative to the longitudinal axis from a substantially straight position. More specifically, the ability to flex allows the approximately 4 mm electrode length to bend between and including 5 degrees to 50 degrees relative to the longitudinal axis from a substantially straight position. Even more specifically, the ability to flex allows the approximately 4 mm length to bend about 45 degrees relative to the longitudinal axis from a substantially straight position.

Figure 24C:
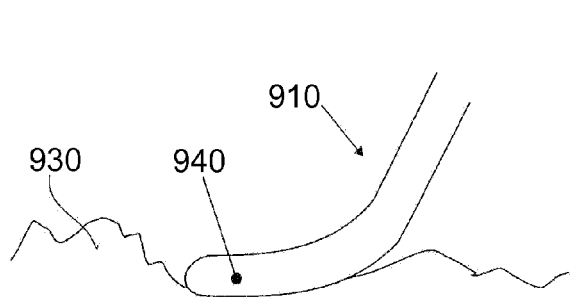
FIG. 24C is a side elevational view of the tip electrode shown in FIG. 24B being dragged across tissue having ridges thereon.
Figure 24D:
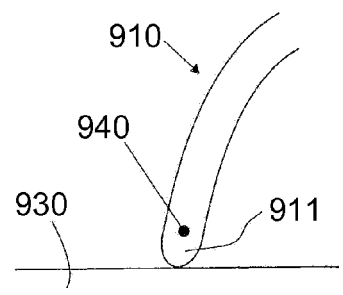
FIG. 24D is aside elevational view of the tip electrode being dragged across smooth tissue surface.

FIGS. 24C and 24D illustrate a flexible electrode 910 being dragged across tissue 930. In FIG. 24C, electrode 910 is flexed and pressed against tissue 930, which has a relatively irregular surface. Being able to flex provides better contact with the target tissue, for example, in the trabeculated endocardial tissue where there are valleys, ridges, and pockets in the tissue surface. Here, electrode-to-tissue contact area is increased by using the side of the electrode 910 to deliver energy for ablation. The increased contact surface increases the likelihood of creating larger lesions at a given contact force and power setting. This in turn enables deeper ablation without having to increase the power setting, which is beneficial because increased power settings undesirably increase the likelihood of coagulation. In FIG. 24D, dome tip 911 is used to delivery energy to tissue 930.

Flexible electrode 910 also capably absorbs any contraction or vibration of tissue 930, and improves continuous tissue contact in a beating heart during systole and diastole, whether the electrode contacts tissue 930 in a parallel, perpendicular, or other orientation. Continuous tissue contact is also assured regardless of whether the electrode is stationary at one location or when the electrode is in motion being dragged. Without such flexibility, a standard rigid tip electrode would "jump off" of the tissue in response to a beating heart.

Optionally, further embodiments of flexible electrodes for catheters may include force-sensing capability to measure contact force with body tissue in different directions. For example, a strain gage, a fiber optic sensor, or other sensor 940 (FIG. 24C) may be disposed within the hollow electrode to measure an amount of force causing the electrode to flex, and to shorten as the case may be. Such data can be collected and communicated to the physician to monitor ablation progress. Monitoring of force experienced at the electrode may, for example, be used to prevent accidental piercing of the target tissue via too much perpendicular force being applied to press dome tip 911 into the tissue.

Unlike known elongated electrodes (e.g., U.S. Pat. No. 6,063,080), which can be laid across a tissue to create relatively longer linear lesions, the flexible electrodes as described have the unexpected advantage of improving precision in mapping and control at specific locations within the heart for more precise ablation, especially in relatively tight anatomical structures. Known elongated electrodes have difficulty positioning in such tight anatomical structures.

One unexpected advantage achieved with a flexible tip electrode is minimized "flipping." When a standard rigid tip electrode is manipulated within a body cavity having valleys and pockets in the tissue, the tip electrode can get caught or stuck in the tissue. As a physician continues to apply force in an attempt to move the tip electrode even though it is caught or stuck, the tip electrode may suddenly "flip" out of the tissue. Such "flipping" is highly undesirable and should be avoided. The proposed flexible tip electrodes greatly minimize "flipping" issues, and allow smoother dragging and motion across valleys and pockets in target tissue.

Figure 25:
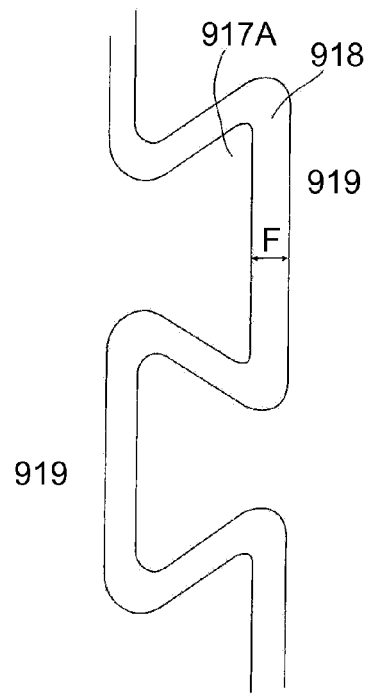
FIG. 25 is a side elevational view of a portion of the tip electrode shown in FIG. 21.

Referring now to FIG. 25, the elongated openings in the wall provide a sufficient elongated gap 918 in the wall to allow shortening of a length of the electrode, when a force is applied to the electrode. Elongated gap 918 extends, for example, between a head 917A and a stem 919 of an adjacent loop in the electrode wall, and allows a freedom of movement F between adjacent stems along the longitudinal axis of the electrode wall when the elongated gap is narrowed or closed. Likewise, elongated gap 918 between adjacent heads 917A provides a freedom of movement F for lengthening of the electrode along the longitudinal length of the electrode when the gap is opened or widened. Such shortening or lengthening may involve widening or narrowing one or more elongated gaps in the various embodiments described above.

In an exemplary embodiment, the electrode can shorten between and including 0.2% to 10% of an axial resting length of the electrode when the elongated gap(s) in the electrode wall are closed. In one embodiment the gap(s) in the electrode wall allows shortening of the axial length between and including 0.1% to 8% of the resting length. More specifically, the elongated gaps in the wall allow axial shortening of the length between and including 0.5% to 5% of the resting length, and even more specifically, the gaps in the wall allow shortening of the resting length between and including 0.1% to 0.5% of the length.

Figure 25A:
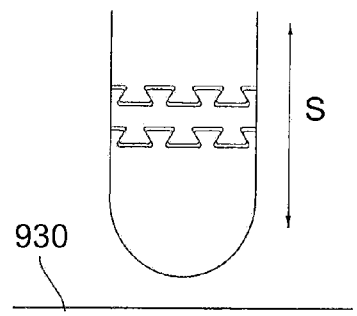
FIG. 25A is a side view of the tip electrode depicted in FIG. 25 at rest.
Figure 25B:
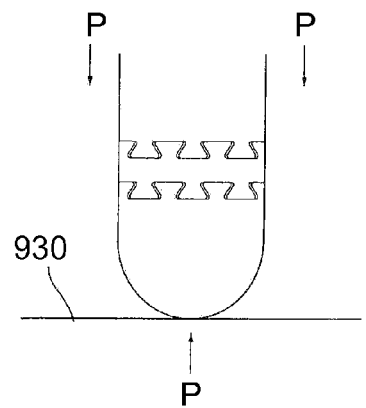
FIG. 25B is a side view of the tip electrode in FIG. 25 when pressed against a tissue surface.

In FIG. 25A, the electrode is at rest where no applied force is exerted thereon, and the electrode assumes a pre-determined shape stretching in the "S" direction and opening the elongated gap(s) to a predetermined amount. When the electrode contacts tissue 930 as shown in FIG. 25B, an applied pressing force P causes the elongated gap(s) to narrow or close and the electrode to shorten, against the stretching force "S." Once shortened, the width of the elongated gap(s) providing freedom of movement F (FIG. 25) in the direction of the applied force P may be minimized as depicted in FIG. 25B. That is, elongated gaps 918 may be fully closed such that the electrode length reaches a minimum axial length that is substantially unaffected by further exertion of applied force P.

In an exemplary embodiment, the stretching force "S" (FIG. 25A) may be provided by a shape memory material or alloy used to fabricate the electrode wall. Alternatively, FIG. 26A shows a cross sectional view of an electrode where the stretching force "S" is provided by a biasing element, such as a spring coil 922, in lumen 920. Coil 922 provides structural integrity to the electrode wall and resiliently maintains the electrode in a pre-determined configuration in a resting state where no applied force is placed on the electrode. In one embodiment, the pre-determined electrode configuration at rest orients the longitudinal axis of the electrode to follow a straight line. In another embodiment, the pre-determined configuration at rest orients the longitudinal axis of the electrode along a curved or arcuate path as shown in FIG. 26B. The contemplated coil resiliently biases the electrode to axially stretch in the direction of arrow S (FIG. 26A) that is generally parallel to the longitudinal axis of the electrode. In other words, the coil optionally biases the tip electrode to stretch lengthwise. When deflected from the pre-determined configuration under applied force, the electrode may resiliently return to the pre-determined configuration when the applied force is released.

Coil 922, or the electrode, or both, may be fabricated from a shape memory material. The flexible tip electrode can be made of suitable conductive and biocompatible materials, suitable for ablation temperature; such materials include natural and synthetic polymers, various metals and metal alloys, Nitinol, naturally occurring materials, textile fibers, and combinations thereof. In one embodiment, the tip electrode is fabricated from MP3SN alloy.

Catheters having flexible tip electrodes such as those described above can optionally be coupled to an irrigation system. That is, the catheter may include a fluid delivery lumen in the tubular catheter body, with the fluid delivery lumen in fluid communication with the hollow electrode. When one or more of the flexible tip electrodes change shape under an applied force, the elongated gap(s) will undergo changes in size and/or shape, thereby affecting the fluid flow therethrough. A cooling fluid, for example, may be pumped in an open flow path through the catheter body to the hollow lumen of the electrode, where it may pass through the gap(s) in the electrode wall to the exterior of the electrode, bathing the electrode and adjacent body tissue with cooling fluid. An internal, closed-loop irrigation system using re-circulated cooling fluid as known in the art is also possible. Also, catheters having flexible tip electrodes can be coupled to an energy source, such as a radio frequency (RF) generator to provide energy needed for tissue ablation. RF signal generators are known and are disclosed, for example, in U.S. Pat. No. 6,235,022.

Flexible tip electrodes for ablation catheters may be formed and fabricated, for example, according to the following methodology. An exemplary method includes providing a hollow cylindrical electrode, and applying a laser to the cylindrical wall of the electrode to cut through a wall of the electrode. The laser cuts the wall in a pre-determined pattern that may extend helically around the circumference of the electrode wall, or may conform to any of the elongated groove or opening patterns previously described in the various embodiments above. As shown in FIG. 27A, the cuts may create an elongated gap 918 that may be consistently wider in some sections M and narrower in some other sections N. The wider sections M may extend substantially laterally from or transverse to a longitudinal axis (such as the axis F in FIG. 24) of the electrode wall. The narrower sections N may connect the wider sections M together, and may be disposed generally in the direction of the longitudinal axis F of the electrode wall.

The wider sections M allow freedom of movement to narrow or widen gap(s) 918 as previously described, making it possible to shorten an axial length of the electrode when a force is applied at a distal end of the electrode towards a proximal end.

FIG. 27B illustrates still another embodiment where the laser also cuts the electrode wall in a predetermined pattern, where the elongated gap 918 created by the laser has generally consistent width. A coil may be subsequently installed in the lumen of this electrode to provide stretching force to create wider sections and narrower sections as previously described in relation to FIG. 26A.

Figure 28:
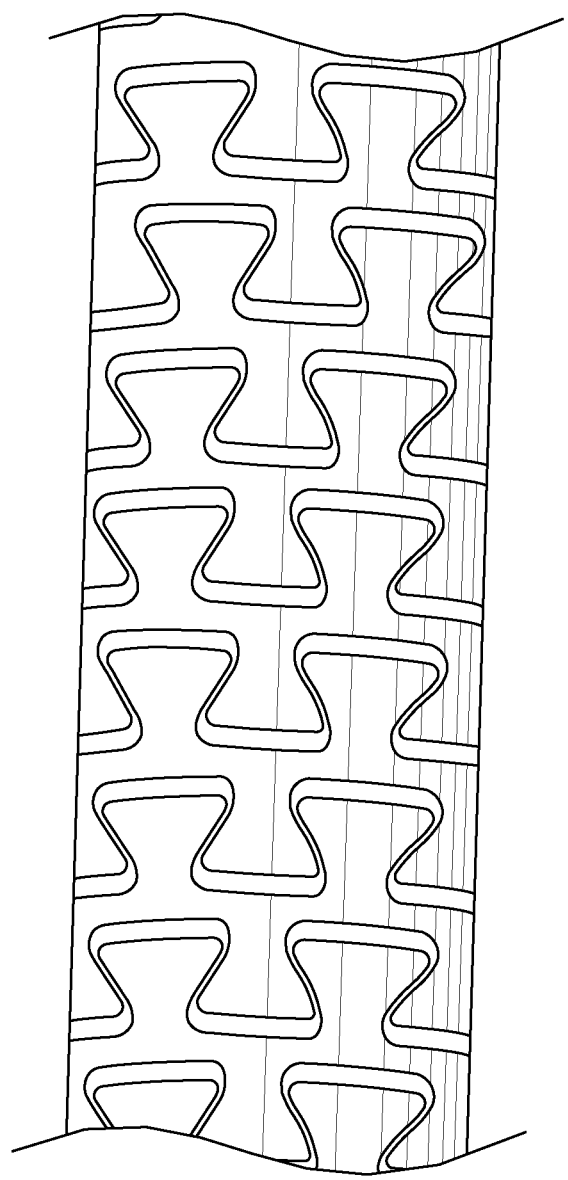
FIG. 28 is a photograph of an exemplary tip electrode.
Figure 29:
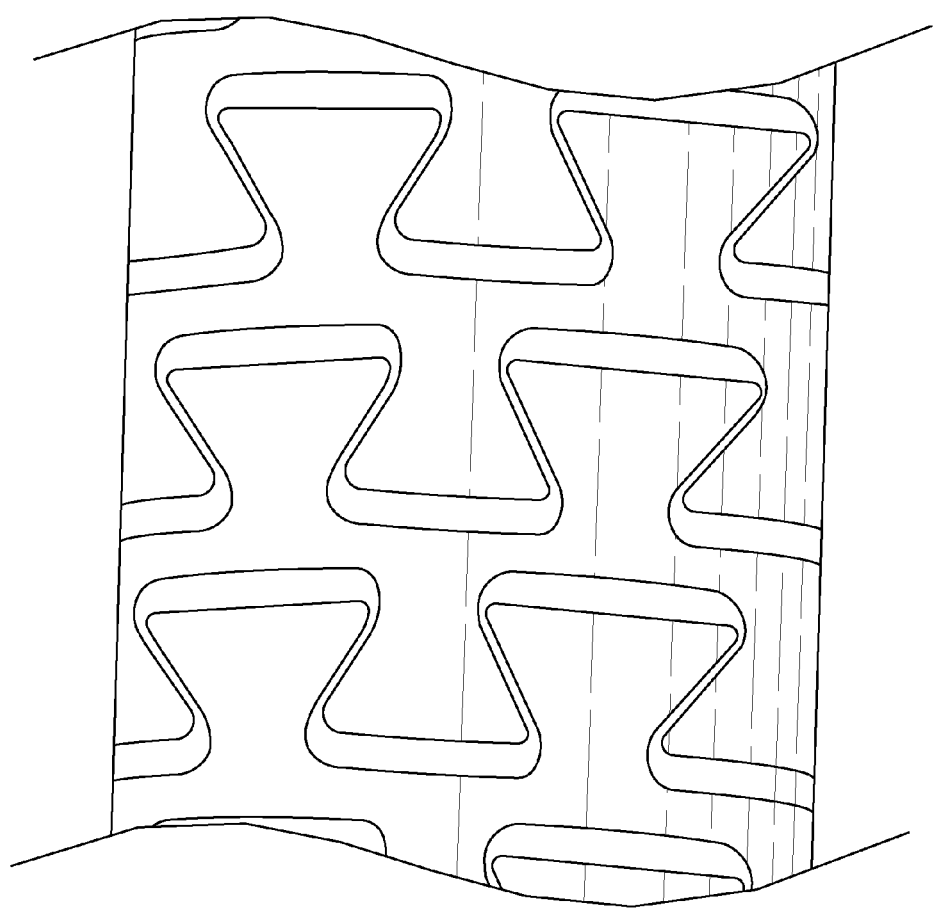
FIG. 29 is a magnified view of a portion of the tip electrode shown in FIG. 28.

FIG. 28 is a photograph of an exemplary tip electrode. FIG. 29 is a magnified view of a portion of the tip electrode shown in FIG. 28. Coatings such as gold and platinum can be applied to the electrode to increase thermo-conductivity of the electrodes. The electrodes can also be coated with heparin to provide anticoagulation effect. In addition, the electrodes may be electro-polished to reduce sharp edges.

The many embodiments of flexible electrodes facilitate the following exemplary methods of performing linear ablation procedures. As with typical ablation catheters, a physician can perform mapping using the electrodes, and determine a target site for ablation. Once determined, the physician may drag the flexible tip electrode across the target tissue to start ablation while applying energy to the tissue. Because the electrode is flexible, the electrode can be more easily dragged across tissue surfaces having ridges and bumps while keeping constant electrode-to-tissue contact. And because the gaps in the electrode wall allows the electrode to be shortened when pressed tip-down against tissue surface, accidental tissue-piercing is largely avoided if not eliminated.

While the invention has been described in terms of various specific embodiments, those skilled in the art will recognize that the invention can be practiced with modification within the spirit and scope of the claims.

What is claimed is:

1. A catheter comprising:
a flexible tubing having a proximal end and a distal end;
an electrode assembly attached to the distal end of the flexible tubing and including a first magnet therein, the electrode assembly including an electrically conductive tip electrode and an electrically nonconductive coupler which is connected between the tip electrode and the distal end of the flexible tubing;
wherein the electrically conductive tip electrode comprises a hollow elongated tip electrode including a sidewall provided with one or more elongated gaps extending through the sidewall, the one or more elongated gaps providing flexibility in the sidewall for bending movement of the tip electrode relative to a longitudinal axis of the flexible tubing, wherein the electrically conductive tip electrode comprises a flexibility that enables it to radially deform such that a cross sectional shape of the tip electrode is changed when the electrode impinges on a tissue surface; and
wherein the first magnet is responsive to an external magnetic field to selectively position and guide the electrode assembly within a body of a patient.

2. A catheter in accordance with claim 1, further comprising a second magnet spaced from the electrode assembly along a longitudinal axis of the tubing; wherein the first magnet and the second magnet are responsive to an external magnetic field to selectively position and guide the electrode assembly within a body of a patient.

3. A catheter in accordance with claim 2, further comprising a lumen passing through the first magnet and the second magnet, and in fluid communication with the electrode assembly, wherein the one or more elongated gaps allow fluid flow therethrough.

4. A catheter in accordance with claim 2, further comprising a third magnet separated from the second magnet by a first distance along the longitudinal axis of the flexible tubing, wherein the second magnet is spaced from the electrode assembly by a second distance along the longitudinal axis of the flexible tubing, the first distance being greater than the second distance.

5. A catheter in accordance with claim 1, wherein the electrically nonconductive coupler and the tip electrode are coupled by an interlocking connection.

6. A catheter in accordance with claim 5, wherein the interlocking connection is formed by coupling an annular projection on the tip electrode and a groove on the electrically nonconductive coupler.

7. A catheter in accordance with claim 5, wherein the interlocking connection is a snap-fit connection.

8. A catheter in accordance with claim 1, wherein the first magnet is disposed in a cavity formed at least partially inside the electrically nonconductive coupler.

9. A catheter in accordance with claim 1, wherein the electrode assembly further includes a band electrode on an external surface of the coupler, the band electrode being spaced from the tip electrode.

10. A catheter in accordance with claim 1, wherein a portion of the flexible tubing distal to the second magnet is more flexible than another portion of the flexible tubing proximal to the second magnet.

11. A catheter in accordance with claim 1, wherein the sidewall is a substantially cylindrical sidewall provided with at least one elongated gap selected from the group consisting of an annular gap around a portion of a circumference of the sidewall and helical gap forming a helical pattern on the sidewall.

12. A catheter as recited in claim 1, wherein the sidewall is a substantially cylindrical sidewall provided with elongated gaps formed therein, the elongated gaps extending as one or more of an annular gap around a portion of a circumference of the sidewall, a helical gap forming a helical pattern on the sidewall, a zigzag gap forming a zigzag pattern on the sidewall, a gap that outlines alternating interlocking blocks, and a wavy gap forming a wavy pattern on the sidewall.

13. A catheter as recited in claim 1, wherein the sidewall is a substantially cylindrical sidewall provided with at least one elongated gap formed therein to provide a freedom of movement and shortening of a length of the tip electrode under an applied force.

14. A catheter as recited in claim 1, further comprising a coil that resiliently biases the sidewall to a pre-determined configuration.

15. A catheter as recited in claim 1, wherein the sidewall comprises a spiraling stem defining opposing interlocking blocks.

16. A catheter as recited in claim 1, wherein the sidewall comprises alternating interlocking blocks disposed on opposite sides of an elongated gap, each block having a head and a neck, and the head being wider than the neck.

17. A catheter comprising:
a tubing having a proximal end and a distal end;
an electrode assembly attached to the distal end of the tubing and including a magnet therein, the electrode assembly including an electrically conductive tip electrode and an electrically nonconductive coupler which is connected between the tip electrode and the distal end of the tubing;
wherein the electrically conductive tip electrode comprises a cylindrical hollow body including a wall, the wall having a pattern of one or more elongated gaps in the wall through a thickness of the wall, the elongated gaps providing axial freedom of movement and allowing the electrode to shorten its axial length when a force is applied to the electrode; and
wherein the magnet is responsive to an external magnetic field to selectively position and guide the electrode assembly within a body of a patient.

18. A catheter in accordance with claim 17, wherein the coupler and the tip electrode are coupled by an interlocking connection.

19. A catheter in accordance with claim 17, wherein the magnet is disposed in a cavity formed at least partially inside the electrically nonconductive coupler.

20. A catheter in accordance with claim 17, wherein the pattern of gaps is selected to shorten the electrically conductive tip electrode between about 0.2% to about 10% of a resting length of the electrode when the force is applied.

21. A catheter in accordance with claim 17, wherein the pattern of gaps is defined by one of an annular gap, a zigzag gap, a gap that resembles alternating interlocking blocks, and a wavy gap.

22. A catheter in accordance with claim 17, wherein the wall is defined by a spiraling stem extending about a longitudinal axis of the electrically conductive tip electrode and forming a series of turns, the gaps being located between adjacent turns of the spiraling stem, and wherein the stem includes a plurality of protruding blocks disposed on both sides of the stem, each block transversely extending towards an adjacent turn.

23. A catheter in accordance with claim 17, wherein the electrode assembly includes a fluid delivery lumen, the fluid delivery lumen in communication with the one or more elongated gaps.

24. A catheter comprising:
a tubing having a proximal end and a distal end;
an electrode assembly attached to the distal end of the tubing and including a magnet therein, the electrode assembly including an electrically conductive tip electrode;
wherein the electrically conductive tip electrode comprises a hollow electrode body defined by a sidewall extending along a longitudinal axis, the sidewall provided with a pattern including one or more elongated gaps through a thickness of the sidewall, the elongated gaps imparting flexibility sufficient to enable the sidewall to radially deform and adopt different operating configurations relative to the longitudinal axis; and
wherein the magnet is responsive to an external magnetic field to selectively position and guide the electrode assembly within a body of a patient.

25. A catheter in accordance with claim 24, wherein the electrode assembly includes an electrically nonconductive coupler which is connected between the tip electrode and the distal end of the tubing, and wherein the magnet is disposed in a cavity formed at least partially inside the coupler.

26. A catheter in accordance with claim 25, wherein the electrically nonconductive coupler and the tip electrode are coupled by an interlocking connection.

27. A catheter in accordance with claim 24, wherein the electrode assembly defines a fluid delivery lumen, the fluid delivery lumen in communication with the one or more elongated gaps.

* * * * *